US008019622B2

(12) United States Patent
Kaboff et al.

(10) Patent No.: US 8,019,622 B2
(45) Date of Patent: Sep. 13, 2011

(54) HOME HEALTH POINT-OF-CARE AND ADMINISTRATION SYSTEM

(75) Inventors: Andrew M. Kaboff, Vernon Hills, IL (US); Steven A. Wegner, Barlett, IL (US)

(73) Assignee: CellTrak Technologies, Inc., Schaumburg, IL (US)

( * ) Notice: Subject to any disclaimer, the term of this patent is extended or adjusted under 35 U.S.C. 154(b) by 998 days.

(21) Appl. No.: 11/586,325

(22) Filed: Oct. 24, 2006

(65) Prior Publication Data

US 2010/0198608 A1 Aug. 5, 2010

Related U.S. Application Data

(60) Provisional application No. 60/729,556, filed on Oct. 24, 2005.

(51) Int. Cl.
*G06Q 50/00* (2006.01)
*G06Q 10/00* (2006.01)
*G01C 21/00* (2006.01)

(52) U.S. Cl. .......... 705/2; 705/7.13; 705/7.15; 701/201; 701/202; 715/741; 342/357.25

(58) Field of Classification Search ................ 705/7.13, 705/7.15; 701/201–202; 342/357.25; 713/150; 715/741, 241
See application file for complete search history.

(56) References Cited

U.S. PATENT DOCUMENTS

| 6,416,471 | B1 | 7/2002 | Kumar et al. | |
|---|---|---|---|---|
| 6,484,033 | B2 | 11/2002 | Murray | |
| 6,865,482 | B2 | 3/2005 | Hull | |
| 6,941,349 | B2 | 9/2005 | Godfrey et al. | |
| 6,980,958 | B1 | 12/2005 | Surwit et al. | |
| 7,197,467 | B2 | 3/2007 | Labadie | |
| 7,259,668 | B2 | 8/2007 | Casey | |
| 7,260,480 | B1 * | 8/2007 | Brown et al. | 702/19 |
| 7,301,451 | B2 | 11/2007 | Hastings | |
| 7,436,311 | B2 | 10/2008 | Rapaport et al. | |
| 7,685,026 | B1 | 3/2010 | McGrady et al. | |
| 2003/0028399 | A1 * | 2/2003 | Davis et al. | 705/2 |
| 2003/0036683 | A1 | 2/2003 | Kehr et al. | |
| 2004/0172301 | A1 | 9/2004 | Mihai et al. | |
| 2004/0260577 | A1 | 12/2004 | Dahlin et al. | |
| 2005/0086072 | A1 | 4/2005 | Fox et al. | |
| 2005/0131740 | A1 | 6/2005 | Massenzio et al. | 705/2 |
| 2005/0222873 | A1 | 10/2005 | Nephin et al. | |
| 2006/0161457 | A1 | 7/2006 | Rapaport et al. | |

(Continued)

OTHER PUBLICATIONS

Gray et al. "A Scalable Home Care System Infrastructure Supporting Domiciliary Care." Department of Computing Science and Mathematics, University of Stirling, Aug. 2007, Retrieved from the Internet: <URL: http://citeseerx.ist.psu.edu/viewdoc/download-?doi=10.1.1.98.4934&rep=rep1&type=pdf>.

(Continued)

*Primary Examiner* — Michael K Collins
(74) *Attorney, Agent, or Firm* — McDonnell Boehnen Hulbert & Berghoff LLP

(57) ABSTRACT

A home health point-of-care and administration system having a server system in communication with a plurality of mobile devices associated with care providers. The server system includes modules for staff scheduling, tracking and travel management, visit record and care plan administration, and communications. The server system bidirectionally communicates with a plurality of mobile devices associated with the caregivers to assist in providing home healthcare services, including the ability to better verify visits by caregivers.

20 Claims, 22 Drawing Sheets

U.S. PATENT DOCUMENTS

| | | | |
|---|---|---|---|
| 2008/0004904 | A1 | 1/2008 | Tran |
| 2008/0033750 | A1 | 2/2008 | Burriss et al. |
| 2008/0040151 | A1 | 2/2008 | Moore |
| 2008/0058615 | A1 | 3/2008 | Clapp et al. |
| 2008/0125959 | A1 | 5/2008 | Doherty et al. |
| 2009/0030731 | A1 | 1/2009 | Reiner |
| 2010/0030578 | A1 | 2/2010 | Siddique et al. |
| 2010/0114941 | A1 | 5/2010 | Von Kaenel et al. |

OTHER PUBLICATIONS

Driver et al. "Facilitating Dynamic Schedules for Healthcare Professionals.", 2007, Retrieved from the Internet: <URL: http://www.tara.tcd.ie/bitstream/2262/16486/1/04205143.pdf>.

Jianyu (Jack) Zhou. "Empirical Tracking and Analysis of the Dynamics in Activity Scheduling and Schedule Execution." University of California, Santa Barbara, Sep. 2006, Retrieved from the Internet: <URL: http://uctc.net/research/diss120.pdf>.

David Krebs. "Wireless Home Care Solutions: Addressing the Quality of Service and Performance Gap." Aug. 2007. Retrieved from the Internet: <UREL: http://na.blackberry.com/eng/campaign/healthcarecampaign/VDC%20wireless%20home%20care%20report.pdf>.

"Home Healthcare Agency Increase Field Accountability with CellTrak and Sprint." 2009 Sprint. Retrieved from the Internet: <URL: http://www.celltrak.com/chca.pdf>.

Breakthrough Tools to Increase Aide Performance Thonberry LTD. Retrieved from Internet 2010. <URL: http://www.thornberryltd.com/index.php?pID=73>.

\* cited by examiner

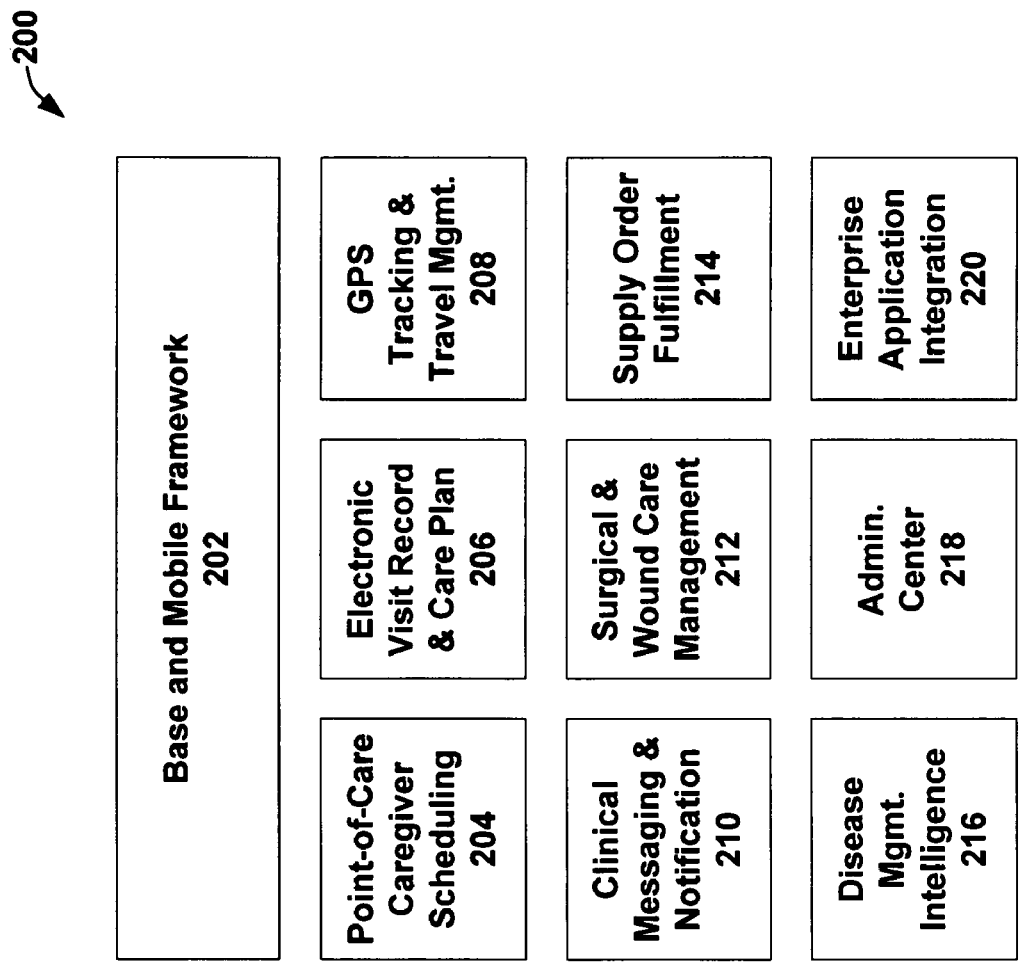

Start Visit
- Automatic Time/Date
- Enter Patient ID#
- Visit Data in Real Time

Visit Capture and Storage
- Real-Time
- Saves Record
- Patient Specific

Error Messaging
- Eliminates Data Errors
- Prompts When Needed

GPS CellTrak
Home Health Services

AIDE VISIT NOTE

Test 1051 Perimeter Drive Schaumburg IL

PATIENT NAME: ▨▨▨▨ MR# 18

Aide Name: Dan ▨▨▨▨

Visit ID: 1
Billable: yes
Date: September 15 2006
Time In: 4:17:46 PM
Time Out: 4:23:10 PM
Total Time: 0:06:24

Vital Signs:
temptation          Axillary
Temp                99.4
bpmicro             Sitting Right Side
bloodpressure       125/59
PainRate            7

Tasks:
BedBath             completed

No Comments

AGENT SIGNATURE _____

HOME HEALTH POINT-OF-CARE AND ADMINISTRATION SYSTEM

RELATED APPLICATIONS

The present application claims priority to U.S. Provisional Patent Application No. 60/729,556, filed on Oct. 24, 2005, titled, "Data Collection, Reporting and Personnel Tracking System and Method," the entire contents (including the source code appendix) of which are hereby incorporated by reference herein.

FIELD OF THE INVENTION

The present invention relates to systems and methods for administering home care, which, in particular, may include, for example, formulating and rendering care plans, collecting and reporting information from field based personnel, and other functions.

BACKGROUND OF THE INVENTION

The home healthcare industry is a multi-billion dollar field. Instead of requiring patients to undergo prolonged hospital stays or frequent visits to a clinic, a home care agency brings the medical services to the patient's location. Payment for services rendered is primarily paid by federal and state Medicare and Medicaid programs. Patient well-being often depends on the visit and attendance compliance of the visiting nurse, aide, or therapist, for example.

Home healthcare agencies dispatch nurses, aides, and therapists to the homes of patients to perform required healthcare assessments, tasks, and other vital services. The frequency and length of time of a visit and the care provided by the visiting professional are important to obtaining a positive outcome and improving the health of the patient. Government reimbursement to a home healthcare agency is paid on a per episode (sickness) basis; therefore, the visiting nurse is often required to recommend the frequency and type of visits by a caregiver. Thus, it is important to ensure compliance by the caregiver in attending the needed visits, and knowing what tasks and services are required for the specific patient. Tracking the duration of the actual visit is also important. Home-care agency administrators are then responsible for processing patient visit data records generated by the visiting staff to be transferred into billing, scheduling, and payroll systems.

Certain home healthcare reporting systems and processes rely on the visiting staff to self report their visit attendance performance. Disadvantageously, at times this results in increased miscommunication, fraud, and abuse by the visiting caregiver. The administrative staff of the home healthcare agency is faced with monitoring the off-site personnel by spot-checking visit attendance data or relying on patient complaints or feedback.

Another disadvantage to such self-reporting procedures is that the reporting is generally self-documented by visiting staff on paper reports. A full time visiting staff employee can perform over 1250 visits a year, which could require a typical administrative staff person to spend an average of five minutes or more per employee visit to process and enter the information into appropriate billing, scheduling, and payroll systems. This can be inefficient and costly. Accordingly, there is a need for a system that provides for improved monitoring, reporting, data communication, and/or tracking of information relating to field service personnel such as visiting staff in the home healthcare field.

BRIEF DESCRIPTION OF THE DRAWINGS

FIG. 2 is a simplified block diagram illustrating representative modules that may be included in an embodiment of the present invention.

FIG. 16 shows a pictorial representation of a display screen for a web portal server computer, showing a "pending visits" details screen, according to one embodiment of the invention.

FIG. 19 shows a pictorial representation of a display screen for a web portal server computer, showing a sample patient report, according to one embodiment of the invention.

DETAILED DESCRIPTION

Figure 1:
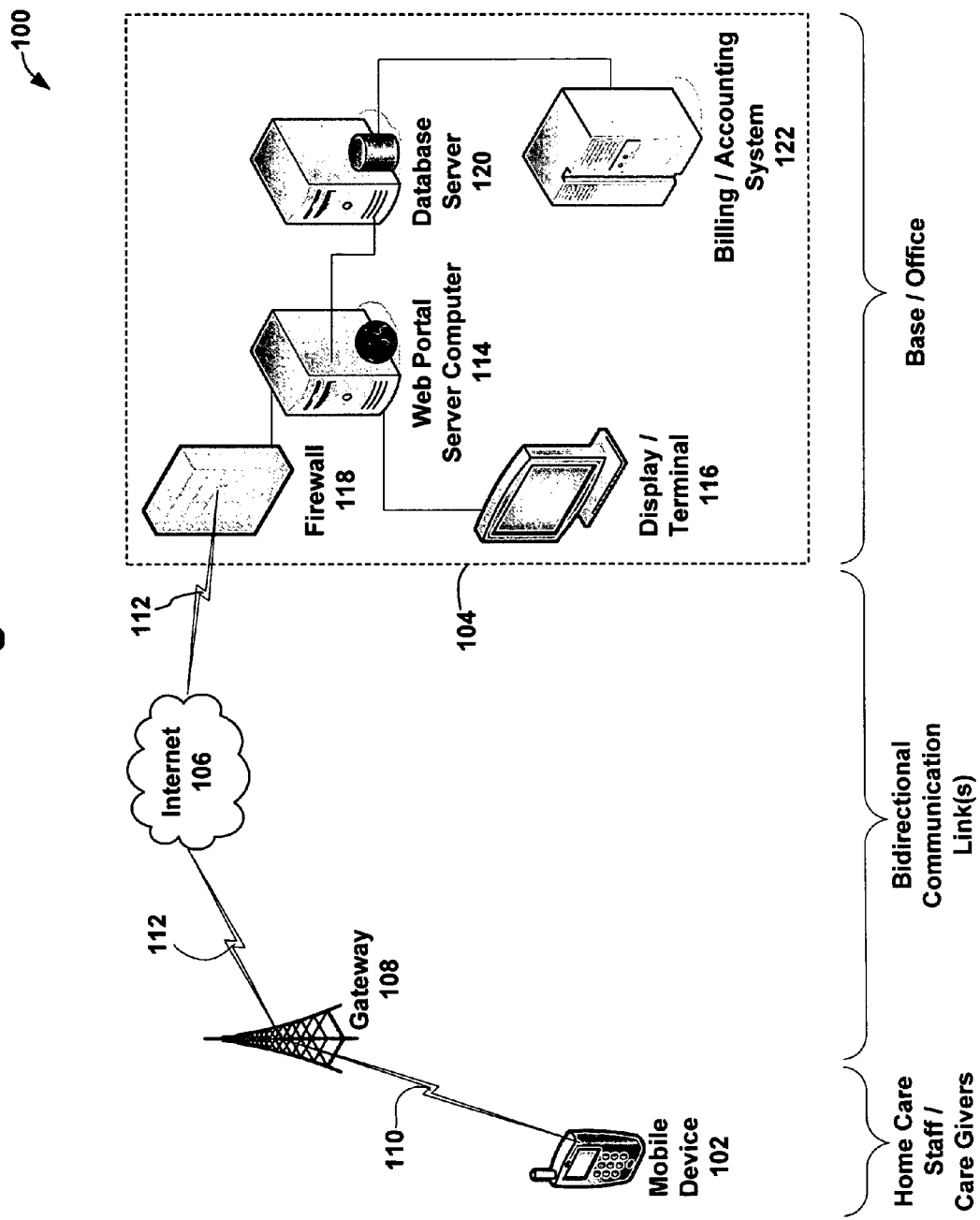
FIG. 1 is a representative system diagram illustrating a home heath point-of-care and administration system according to an embodiment of the present invention.

A home health point-of-care and administration system is provided that, in various embodiments, may track visiting staff members during working hours via a global positioning system (GPS) and further prompt the visiting staff to electronically interact with software-based tracking and data communication programs associated with a mobile device, such as a mobile or wireless telephone or other communication device. The tracking and communication programs associated with one or more computer-based communication devices provide for bi-directional communication and build a patient visit record dynamically based on the specific services required for the patient. For example, the visiting staff may enter a patient record number, alpha numeric data, or other data into the mobile device via an input device, such as a keypad, touchscreen, or other device, to start a visit. A visit record is, in turn, generated and transmitted to an office administration server system over a communication network such as the Internet and alerts the administration that a visit is starting for a specific patient. In one example, the server system automatically responds to the visit that is starting and sends back to the visiting staff member's mobile device the specific list of tasks, vitals, and services to be performed for the patient. Alternatively, information and task instructions may be manually inputted by an administrator and sent to the visiting staff member.

By receiving this information from the administrative computer-based server system, the visiting staff member knows specifically what patients are on his or her schedule, an optimized route to take to visit each patient, what to do for that patient, and a patient specific visit record may be generated. The administrative staff persons at the home office (server system) are informed that a visit has started, of the time and date it started, of the staff person that is performing the homecare visit, and what the visiting staff person was told to do for the specific patient. By way of example only, the present specification describes embodiments related to systems and methods of data collection, reporting and tracking of in-field home healthcare personnel. However, it is understood that the present invention may encompass and apply to various systems and methods and is intended to relate to alternative embodiments for use in communicating information with, and the monitoring of, any type of field service personnel.

The home health point-of-care and administration system starts a visit by creating a patient and visiting staff electronic visit record at the point-of-care. The record may selectively be customized to each specific patient each time a new visit is started. The record allows the visiting staff person to enter patient-specific vitals, identify patient conditions, report service performed and a clock associated with the mobile telephone communication device independently records the visit time, and provides it in the visit record. Preferably, the mobile telephone communication device employed by the visiting staff user is capable of communicating data over the Internet. The communication device may alternatively be any type of telephonic device, personal digital assistant (PDA), personal computer (PC), or any other type of bi-directional communication device capable of transmitting and receiving data. The communication device is preferably a computer software-based device that has an associated memory for storage of data communication software and personnel/device tracking software. It is understood that the communication and tracking software can be operated on various types of mobile or cellular telephones, personal digital assistants (PDA), portable personal computers (PC) or any type of mobile device capable of conducting bi-directional communications that can receive and enter alpha and numeric data from a field location such as at the point-of-care location of a patient. The completed visit record is then electronically sent by the mobile device over the Internet (or other communication network) to a server system and the open visit record in progress is automatically filled out and completed. A real-time paperless dynamic patient specific record is accordingly provided to appropriate administrative staff that may include, for example, vital patient data in real-time. Provision of this record in real-time tends to reduce errors, expedite the data entry, reduce expenses and improve patient outcomes and reduces the chances of staff fraud and abuse.

In one aspect, the system provides electronic data collection and reporting. Interaction with the communication device, such as a wireless portable telephone, by the user establishes a visitation record through real-time data communication with the application server computer. A complete visit compliance record is created in paperless fashion and real-time confirmation of a completed visit is provided. A global positioning system (GPS) is also associated with the communication device (as well as the server system) and provides for real-time tracking and recording of the user (such as visiting homecare staff personnel) and is able to determine a traveled path of the user. Estimated speed and length of travel are used in conjunction with the GPS application for automatically calculating accurate mileage of the user. User travel is tracked from location to location such that mileage to the $100^{th}$ of a mile may be determined. A shortest distance from location to location as the user is traveling between visits may be determined. The travel path between locations or visits is automatically determined and recorded in real-time for accurate mileage recordation.

Figure 6A:
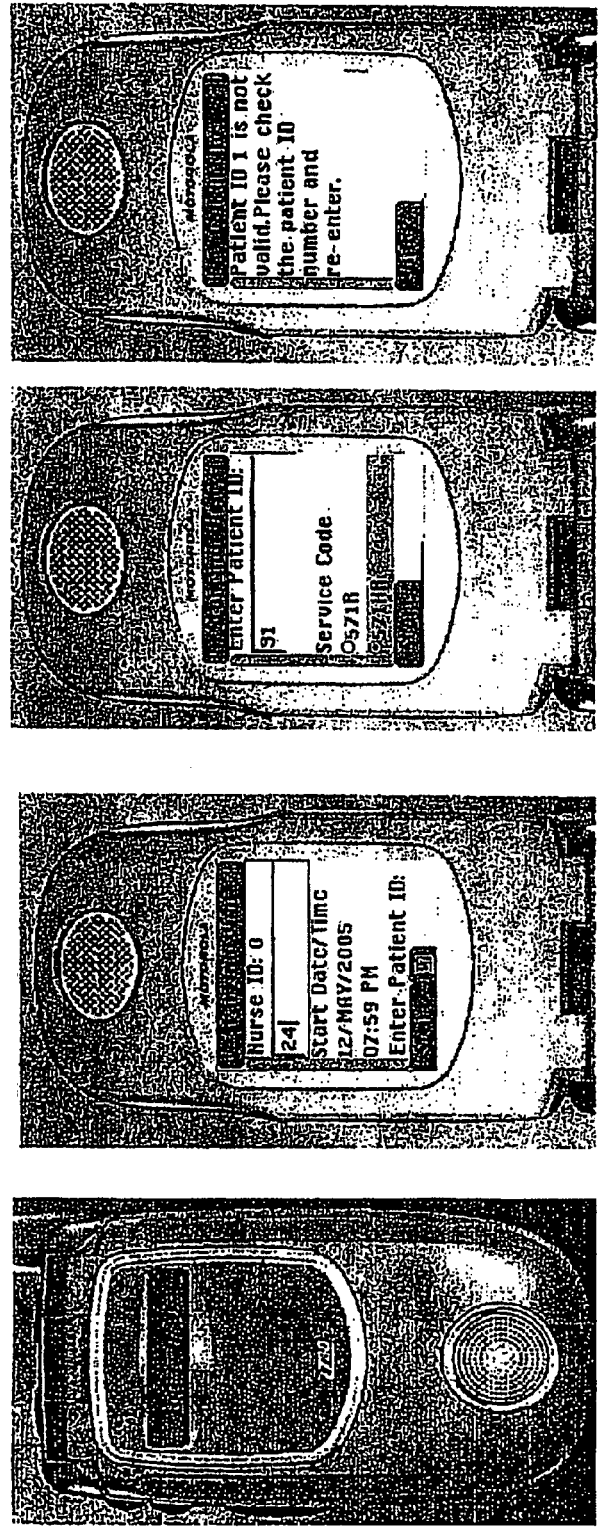
FIG. 6A shows pictorial representations of a display screen for a mobile device, showing an initialization procedure, according to one embodiment of the invention.
Figure 6B:
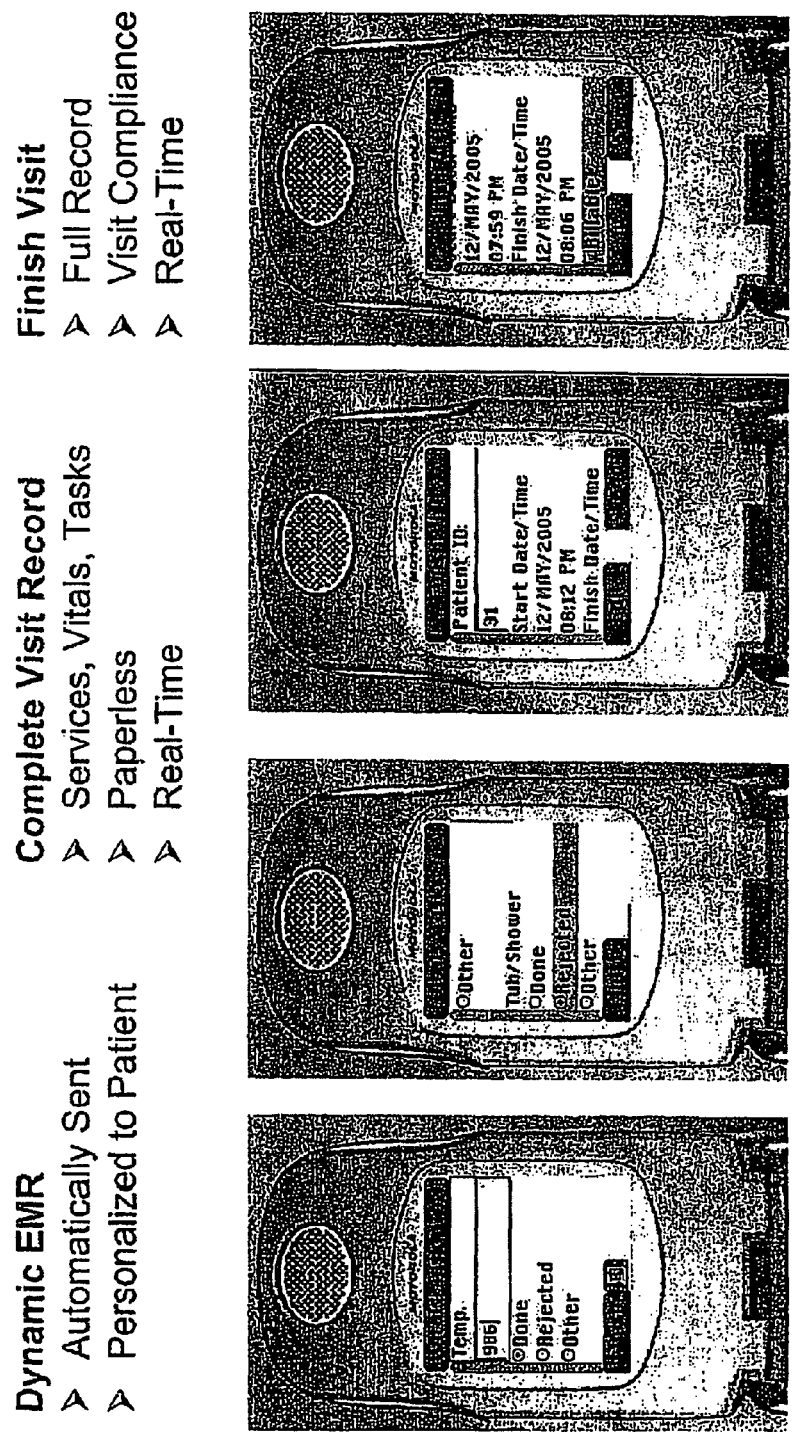
FIG. 6B shows pictorial representations of a display screen for a mobile device, showing data inputs to complete tasks and a conclusion procedure, according to one embodiment of the invention.

In one example, the communication device employed includes a keypad, touchscreen, or alternative input device for inputting information into the computer memory of the communication device. The communication device is a computer software-based unit having a clock for automatically keeping track of time and date information. When the user begins or starts a visit, for example to the home of a patient, the user may move through a menu provided on a screen of the communication device and select a "start visit" application through interaction with the input device. The user may then enter an identification number associated with the patient or enter other related visit data which is recorded in real-time. Once the visitation is started and the time and date information is recorded, the user may input various information relating to the patient in response to various prompts that appear at the display of the communication device, as seen in FIGS. 6A and 6B.

The software-based client application associated with the communication device, that is operated by the user, provides various screen displays or prompts to the user at the start of a visit. Additionally, the client applications will provide displays to the user related to the assignment of various tasks to be performed by the user during the in-field activity (e.g. during a patient visit). The displays or prompts provided by the client application instruct the user to input information related to the in-field activity such as information related to a patient and a patient visit (see FIGS. 6A and 6B). Various tasks are performed and completed by the user and certain requested information is inputted and stored in memory of the communication device. Once the tasks are completed and the user inputs necessary information, for example information relating to a patient and a patient visit, the client application may provide a finish visit prompt (e.g. providing a "finish" display on the display screen) to end the visit and complete recordation of the associated information related to the visit. Time and date information are recorded as well as the information accumulated in relation to the visit. Such information associated with the visit may be stored in memory at the computer-based communication device for transmission to a remote server system.

The data information inputted and accumulated at the client communication device is transmitted through a communications network, such as the Internet, and is recorded at a server system. As discussed, the visit information is captured and stored in real-time. A record is created and saved relating to the visit (for example a patient specific record containing information associated with the patient visit) and may be used for administrative purposes. The server system may include a web portal computer for establishing proper communication through the Internet or World Wide Web with the communication devices operating in the field. The web portal computer may be coupled to an office/administrative computer or, alternatively, to a display unit for retrieval and viewing of the record information stored that has been received from the in-field communication devices. The web portal computer (either alone or in conjunction with other computers or display devices) may provide for the viewing of open visits. An administrator reviewing such records may view, edit or approve of visits and the tasks performed during visits as the information is received by the server system in real-time. Alternatively, such editing or approval of information relating to visits may be performed in an automated fashion by the web portal server or by other computer devices associated therewith. The records established with completed visits (such as records involving home care patient visits) are archived at the server system. The server system may further provide reporting capabilities. Thus, from the communication device, a dynamic electronic record that is personalized to a patient, patient visit or other in-field activity is automatically sent via the Internet for receipt by a remote server system.

The information is sent in real-time (and in a paperless fashion) such that a detailed electronic visit record is provided. For example, for a home visit of a patient, the established record reflecting the visit may selectively include information relating to the services and tasks performed, the vitals obtained relating to the patient, the start/finish times of the visit, information relating to billing, information relating to the in-field health care person using the communication device, and any other information associated with the visit. The real-time bi-directional communication between the server and the communication devices in the field allows for proper visit compliance to be achieved and detailed paperless records to be established for individual visits, which may then be used for monitoring, billing, reporting or other administrative purposes.

Figure 6C:
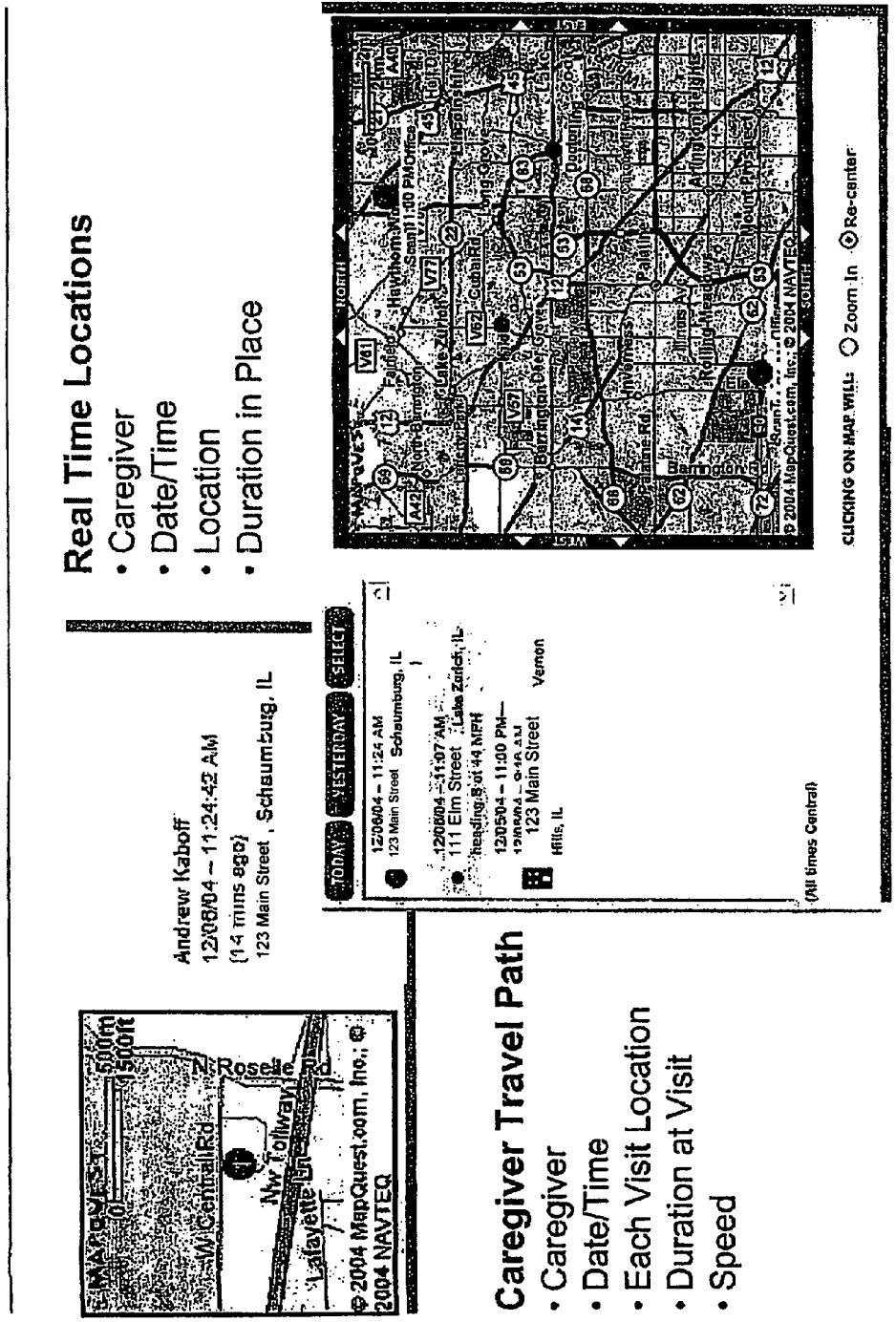
FIG. 6C shows a pictorial representation of a display screen for a web portal server computer, showing a map-based tracking application, according to one embodiment of the invention.

As described herein, the home health point-of-care and administration system includes a GPS application for real-time tracking and recording of off-site personnel as they perform tasks in the field. The GPS application allows for monitoring, from the remote server system (or alternative office or computer-based monitoring location), of the position or location of the field staff members as they possess and carry associated communication devices with them from visit to visit. The GPS application is programmed to identify the daily path of travel as the field personnel users transport their respective communication devices with them as they move from each visit location. The GPS application determines the location coordinates of the communication device held by the off-site personnel user and sends the coordinates from the communication device to the remote server system, for example, at predetermined time intervals such as every two minutes. The tracking performed by the GPS application provides for real-time web mapping and accurately tracks the device location within a particular distance range (e.g. 300 ft.) Automatic geofencing of different locations (such as different patient homes) may selectively be performed. The GPS component of the system allows for real-time communication of location information to the remote server system including date/time information, as well as location and duration in place for the visiting staff member. The travel path of the visiting staff member is also mapped out for display at the remote server system and information such as: date and times, each visit location, duration at each visit, and travel time/speed are selectively provided, as seen in FIG. 6C.

Referring now to FIG. 1, one embodiment of a home health point-of-care and administration system 100 includes one or more mobile devices 102 that may be used by a home-care staff person and/or caregiver to bidirectionally communicate 110, 112 with base/office server system 104. The bidirectional communications 112 are preferably over the Internet 106, which the mobile device 102 may access through a gateway 108. The preferred protocol used to communicate data is HTTPS (HyperText Transfer Protocol with SSL (Secure Socket Layer) encryption for security).

Where the mobile device 102 is a cell phone, the gateway 108 may comprise a cellular tower, base station, and Internet gateway, so that the mobile device 102 communicates with the gateway 108 via a cellular signal 110. Other alternatives for facilitating wireless bidirectional communications could call for the gateway 108 being a wireless gateway at a patient's home or a private or municipal WiFi access point. As yet another alternative, the mobile device 102 may be a satellite phone, and gateway 108 could include a satellite communication system that provides access to the Internet 106. The particular implementation of the bidirectional communication link between the mobile device 102 and the server system 104 may vary depending on what systems are available in the relevant home care region being serviced. The frequency of data transmissions will depend on the particular activity that is in process; however, a typical schedule might be a morning download to obtain schedule information, along with periodic transmissions as visits are completed. For example, a home infusion therapy visit might call for relatively infrequent transmissions (e.g. batch files transmitted three times per day), since an infusion is generally a slow process, with relatively little data to report. In contrast, a battery of clinical measurements performed by a nurse's aide may be transmitted after each measurement is taken, for real-time reporting, which can be useful if disease management intelligence is included in the system (see FIG. 2, module 216).

The mobile device 102 is preferably a small (easily portable) wireless device that includes at least a display and a data entry mechanism, such as a keypad, keyboard, touch-screen, and/or voice-recognition input system. Other physical features that may be included as part of the mobile device 102 are (a) a transceiver, such as a cellular phone and/or wireless modem (data transmissions would preferably made using a cell phone's data plan), (b) an imaging device, such as a digital camera and/or video camera, (c) a GPS (Global Positioning System) module, (d) an RFID (Radio-Frequency Identification) module, and/or (e) a Bluetooth (or other PAN (Personal Area Network) module. The mobile device 102 is preferably carried by each home-care staff person and/or caregiver that operates in the field. These may include, for example, nurse aides, nurses, therapists, physician assistants, and other medical technicians and/or professionals.

To provide the functionality afforded by various embodiments of the present invention, the mobile device 102 preferably includes software, hardware, firmware, or a combination of these, to allow the mobile device 102 to act as a client device with respect to the server system 104. As such, the mobile device preferably includes one or more resident software applications and associated data storage so that the mobile device can be configured to provide one or more of the following example features:

- Require a user to enter a username and/or password to prevent unauthorized access to the mobile device and underlying accessible patient data;
- Exchange, update, approve, and/or deny staff schedules with the server system 104;
- Transmit position updates to the server system 104, using the GPS module;
- Accept a patient identification input from the user for an upcoming or current visit to the residence or current location of a particular home care patient;
- Download from the server system 104 a patient-specific care plan corresponding to the particular home care patient;
- Dynamically render on the mobile device 102 one or more electronic data collection forms corresponding to the downloaded care plan;
- Prompt the user to enter data corresponding to the electronic data collection forms;
- Accept and validate data entered into the electronic data collection forms by the user;
- Receive transmissions from telemedicine devices, such as Bluetooth-enabled weight scales, pacemakers, blood-pressure monitors, and others;
- Transmit the entered data and/or completed electronic data collection forms to the server system 104;
- Upon determining that no communication link is present, storing entered data offline (on the mobile device) for a period of time, until a communication link is again present;
- Receive and display clinical messaging and/or notification from the server system 104;
- Capture clinical images and/or video of patient features, such as surgical and wound conditions;
- Accept voice annotations from the user, where the voice annotations may be associated with the captured clinical images or other data inputted by the user into the mobile device;
- Accept supply order requests from the user and transmit the supply order requests to the server system so that they may be fulfilled; and
- Receive messages and alerts from the server system 104 that relate to real-time health conditions for a patient undergoing a home care visit.

The above features are merely examples of some of the functionality that may be provided on the mobile device 102, in accordance with various embodiments of the present invention. These features may be supported by a set of application components written in programming languages such as mobile computing languages (e.g. J2ME or BREW), running on the mobile device 102.

The server system 104 in the illustrated embodiment includes a web portal server computer 114 and one or more associated displays 116, a firewall 118, one or more database servers 120, and a billing/accounting system 122. The server system 104 may be a centralized nation-wide central system that provides administration services for several or many home care offices in different regions. Alternatively, each home care region could be serviced by one or more dedicated server systems 104. Multiple server systems 104 and/or multiple components within the server system 104 may be included in order to provide redundancy and/or load balancing.

The server computer 114 acts as a server to the mobile device 102 and is preferably provided with a software based web server application that performs many actions such as dynamically managing workforce schedules; viewing open visits; viewing, editing and approving visits; archiving completed visits; and reporting based on monitoring and communicating visit information with the mobile device 102 used by caregivers and or other home-care staff in the field. Since bidirectional communications with the mobile device 102 are preferably made over the public Internet 106, the server computer 114 is preferably connected to the Internet 106 through the firewall 118.

The one or more displays/terminals 116 may be used by office-based staff to create, modify, and otherwise interact with care plans, patient information, staff schedules, and other data. Examples of such devices 116 include desktop PCs, laptop computers, Tablet PCs, workstations, or any computer devices running on any Operating System that can connect to a World Wide Web server, retrieve, and display web pages.

The database server 120 may selectively store various types of data that provide assistance in the management and administration of information, such as visit records and field service monitoring reports, obtained as a result of activities (such as home care visits) performed by field service personnel or agents. The database server 120 may be coupled to a local or remote corporate billing/accounting system 122 to provide appropriate billing information based on tasks performed by the field service personnel. A non-exclusive list of the types of information (fields) that may be stored in one or more databases includes: patient demographic information, home care tasks, staff information, locations, visit records, visit status, care plans, actual tasks that are performed in each actual visit, clinical outcomes, and clinical measurements. The one or more databases are preferably of any RDBMS (Relational Database Management System) based. For example, a care plan may be maintained as a table having rows and columns corresponding to the stored fields. XML (eXtensible Markup Language) based data structure with associated tags and metadata are preferably used for storing and sharing the home care information among the components of the system 100.

FIG. 2 is a simplified block diagram illustrating representative modules 200 that may be included in an embodiment of the present invention. The modules include an underlying base and mobile framework module 202 and a plurality of functional modules 204-220. Each of these modules will now be described in order. While all of the representative modules 200 may be included in certain embodiments of the present invention, some embodiments may be omitted in alternative embodiments, depending on the particular functionality to be provided by the home care administration system.

Base and Mobile Framework

The base and mobile framework 202 is the foundation layer of the home care administration system 100 and is what allows the other modules 204-220 to operate. Based on the framework 202, applications in the system 100 are designed and tuned to provide optimal performance in the mobile home care and home health settings. For example, the framework includes, but is not limited to, components such as dynamically rendering data collection forms on the mobile device 102; dynamically rendering applications from the server system 104 to the mobile device 102; and managing data types, rules, validation, offline data storage, security, and data transmission between the mobile device 102 and the server system 104.

For example, dynamic rendering of data collection forms on the mobile device 104 may include the appearance on the mobile device 102 of a particular electronic fillable medical form to be filled out by a caregiver during a patient visit. In legacy systems, such as paper-based systems, forms were often designed to look the same regardless of what tasks were to be performed for a particular visit, in order to promote uniformity and prevent mistakes in complying with standards set by Medicare and other organizations. However, the framework 202 provides a patient-specific, visit-specific form for each visit to a patient. While further details are provided elsewhere in this specification as to how the content for such a form is generated, the framework 202 includes components in the mobile device 102 and/or server system 104 that transmit at least an indication of this content from the server system 104 to the mobile device 102, so that the mobile device 102 will display a fillable form that includes only the patient-specific, visit-specific tasks to be performed.

At least two possible techniques for rendering forms on the mobile device 102 vary in the amount of processing performed by the mobile device 102 versus the server system 104. A first technique is for the server system 102 (and, in particular, an application on the server computer 114, to send task metadata to the mobile device 104. The task metadata could indicate, for example what specific tasks are to be performed and the kind of data expected to be entered in response to performing those tasks (e.g. numbers, characters, integers, binary inputs, or even particular expected ranges, such as a range for body temperature or blood pressure). A second technique would be for the server system 104 to create the form on the server side and send the created form as a fillable patient-specific, visit-specific form to the mobile device 102. The application on the mobile device 102 would then display the fillable form and accept data entries from the caregiver. The decision of whether to use the first technique or the second technique, or a variation of either one, will depend on several factors, such as the bandwidth of the transmission media (e.g. 110, 112), the processing capabilities of the mobile device 102, and other factors. The presently preferred embodiment utilizes the first technique to account for relatively slow transmission rates supported by many current cell phone systems. The term "fillable form" is intended to broadly compass text prompts, a graphical form, audio prompts, and other forms for collecting data.

Dynamic rendering of applications from the server system 104 to the mobile device 102 allows application(s) on the mobile device 102 to be updated and/or supplemented without frequent recompilations. By specifying, through use of the server system 104, client or company specific requirements, (such as graphical menus, layouts, widgets, and data) a mobile application may be built or rendered on the fly. The server sends the actual application as well as the metadata concerning the visit-specific form.

Managing data types, rules, validation, offline data storage, security, and data transmission are other tasks that are preferably handled by the framework 202.

Since the system 100 is designed to present the caregiver with fillable patient-specific, visit-specific forms, it becomes beneficial to assess the data being entered by the caregiver into such forms. By sending metadata to the mobile device 102, the server system 104 can provide instructions on how the application on the mobile device 102 treats data and what kind of data is expected (e.g. a particular range for a blood pressure reading). Expected data types may include, for example, number, character, integer, binary value, etc. In addition, the metadata might also include one or more rules for at least some of the data entries made by the caregiver. An example of a rule is that an entered pulse rate cannot equal zero or a negative number. Finally, to ensure that the entered data matches the expected data, validation can be performed to check the entered data values against the rules.

Offline data storage may be necessary in at least two cases: while the mobile device 102 is out of wireless data service coverage, so that the data needs to be stored until coverage is present again, and (2) when data has just been collected and entered into the mobile device 102, but not yet transmitted to the server system 104. Such offline data storage is preferably in memory or some other storage medium that maintains its contents even if the device 102 is powered down.

Security may include at least two aspects. A first aspect is directed to assessing whether the possessor/user of the mobile device 102 is authorized to access the mobile device 102. This assessment could include requiring the user to enter a PIN (Personal Identification Number) or username and password, for example, when the mobile device 102 is turned on or a home care application is started up on the mobile device 102. This is to prevent an unauthorized user from accessing (1) applications pertaining to the system 100, and (2) offline data that may be stored on the mobile device 102. Such offline data could include, for example, clinical patient measurements that have been stored offline (on the mobile device 102) while the mobile device 102 is out of wireless data service coverage or even data that has just been collected and entered into the mobile device 102, but not yet transmitted to the server system 104. The second aspect is directed to protecting data as it is communicated across communication links 110/112. The second aspect may be addressed by encrypting the data and deleting offline data from the mobile device 102 once it has been sent to the server system 104.

Point-of-Care Caregiver Scheduling Module

The point-of-care caregiver scheduling module ("scheduling module") 204 enables the home care office and caregivers to dynamically create, publish (provide appropriate notification), and synchronize schedules bi-directionally in real-time, while caregivers are in the field. There are two aspects to these scheduling functions. First, as opposed to being only static, the scheduling module 204 allows a caregiver's schedule to change while the caregiver is in the field (e.g. conducting a visit at a patient's home). For example, while a first caregiver is conducting a visit at a first patient's home, the home office might receive notice that a second caregiver has become ill and will be unable to complete his or her previously scheduled visits. The home office can then update the first caregiver's schedule so that the first caregiver can cover the visits that the second caregiver was previously going to conduct. The first caregiver will then receive notification of the updated schedule and can go to the next patient's home accordingly. As another example, caregiver schedules might be changed if a worker at the home office notices that several visits are in a particular area or location (e.g. at a single nursing home), so that it would be more economical and efficient for a single caregiver to conduct all the visits for that data at that particular location. A second aspect to the scheduling functions handled by the scheduling module is its bidirectional nature. Workers in the field (e.g. caregivers) are able to set schedules according to predefined rules. For example, if this functionality is present and enabled, a higher-skilled worker (e.g. nurse) might set the schedule of a lower-skilled worker (e.g. nurse's aide), either directly or by updating his or her own schedule. If a nurse updates her schedule to conduct a wound-inspection visit with a burn victim, such an update might also include updating the schedule of a nurse's aide to visit the same patient at the same time or directly after, to apply new bandages, for example.

In a preferred embodiment, the point-of-care caregiver scheduling module acts as a workforce management system that generates work schedules dynamically based on a plurality of worker-based variables, patient-based variables, or other variables. Example worker-based variables include (1) a worker's location, (2) a worker's expertise level, and/or (3) whether a worker has previously conducted a visit at a particular location. Example patient-based variables include (1) a patient's location, (2) a patient's care plan or medical plan status (e.g. covered services/timing versus non-covered services/timing), and/or (3) a patient's disease-state or condition. The workforce management system may be particularly beneficial where an appointment is cancelled and a worker needs to be efficiently rescheduled, in emergency situations, where a worker needs to be rescheduled because of a change in a patient's disease-state or condition, or in the situation where a patient's insurance coverage would expire after a certain date so that a visit should be conducted before expiration.

The aforementioned workforce management system preferably interfaces with the GPS tracking and travel management module to obtain worker location information. Patient information, such as location information, may be obtained from home office records (such as a patient database), for example. Dynamic generation of schedule information based on location information may be accomplished by selecting visits in order to minimize a travel-route cumulative distance, as determined by accessing maps databases, such as those offered by NAVTEQ or Tele Atlas NV, for example.

Electronic Visit Record and Care Plan Module

The electronic visit record and care plan module 206 preferably comprises software applications located on the mobile device 102 and at the server system 104 (such as on the server computer 114) for electronically creating, storing, communicating, and monitoring information on patients, visits, tasks, care plans, and other home-care-related information. Legacy systems typically were paper-driven and labor intensive, due to the prevalence of paper forms that were generic, rather than patient-specific and/or visit-specific. In contrast, the electronic visit record and care plan module 206 provides customizable care plans that may be downloaded in real-time to a caregiver's mobile device 102. Customization may include, for example, the ability to add tasks to a visit "on-the-fly," such as throughout a particular patient's overall home care period, as the patient's condition improves, declines, or otherwise changes. In addition, different tasks can be added by different supervisory care persons, such as nurses, doctors, or therapists, to be performed by the caregiver in the field. Such care plan customization may be accomplished, for example by presenting a care plan administrator with a user interface identifying a plurality of tasks that be selected, such as through check-boxes that the administrator may select. (See FIG. 8.)

When used in conjunction with the scheduling module or a variation thereof, the electronic visit record and care plan module 206 can be utilized to deliver the patient-specific, visit-specific care plan to the correct caregiver at the correct time and place (such as when the caregiver is arriving at the patient's home). When used in conjunction with the GPS module 206 (described below), the electronic visit record and care plan module 206 may receive a notification that the caregiver's location is close to or the same as the patient's location, which can serve as a "transmit initiation" signal indicating that that particular patient's care plan should be sent out to the caregiver at that location (as determined by the GPS module 206) (i.e. "pushed" by the server system 104 to the mobile device 102). In embodiments lacking the GPS module 206, the caregiver may simply enter a patient ID to cause that patient's care plan to be transmitted (i.e. "pulled from the server system 104"). Alternatively, the care plan for a particular patient may be transmitted at a particular time, as maintained by the scheduling module 204 (i.e. "pushed" by the server system 104 to the mobile device 102).

In addition, the electronic visit record and care plan module 206 helps to ensure that the visit record (the data entered by the caregiver into the fillable form or the filled form itself) matches the individualized care plan. As a result, no extra tasks are performed (saving time and expense) and no tasks are omitted without reason (promoting the patient's well-being and saving extra expenses associated with extra patient visits to complete omitted tasks). This also helps to ensure compliance with organizations and packages requiring standardized formats, such as those reporting records required by Medicare and other reimbursing organizations. Service codes and billing exceptions and required records (e.g. HHA records) can be generated automatically.

Another function that can be performed by the electronic visit record and care plan module 206 is to validate data entered by the caregiver. Validation is basically comparing the collected (entered) data with built-in user-defined business intelligence and/or rules that can be specified by a user, such as a home care administrator or health care professional. An example of business intelligence is an allowable range for a blood pressure reading. Thus, when a high blood pressure reading is taken, the caregiver may be instructed by the application on the mobile device 102 (or through messaging from the server system 104) to call a particular nurse or to give patient-specific health and wellness instructions. Thus, while the data may technically be the correct type of data (e.g. an integer) as called for by a particular rule, it may still be acted upon by the business intelligence to generate an alarm condition (e.g. call nurse). Rules and business intelligence can be communicated by metadata, as discussed above with reference to the base and mobile framework 202.

Yet another function that may be supported by the electronic visit record and care plan module 206 is to interact with telemedicine devices. A telemedicine device may take and/or record measurements from a patient and either (1) transmit those measurements in real-time to the mobile device 102 or (2) store measurements until a certain condition is satisfied, such as a caregiver visit is taking place, before transmitting (non-real-time). A PAN (Personal Area Network) technology, such as Bluetooth, may be used for communications between the telemedicine device and the mobile device 102. Examples of such possible devices are scales, pacemakers, and blood pressure monitors, among others.

Finally, the electronic visit record and care plan module 206 can be used to assign or attach multiple care plans to a single patient. In a sophisticated home care system, a single patient may have more than one caregiver. For example, an elderly patient being treated at home for a fractured hip caused by a recent fall may be visited by both a nurse and a physical therapist, both of which are likely to provide different types of care. These different care types can manifest themselves through two different care plans comprising different sets of tasks selected to be performed by the caregiver.

GPS Tracking and Travel Management Module

The GPS tracking and travel management module ("GPS module") 208 can be included in various embodiments of the invention to assist in tracking home care providers, presenting actual driving mileage traveled by a caregiver along with a shortest route indication and shortest mileage, tracking actual visit times, and alerting missing or delayed visits as exceptions. In order to offer this functionality, the mobile device 102 needs to be equipped with a mechanism for determining its current location, such as a GPS receiver. Many cell phones manufactured today and in recent years include a GPS receiver in them, which can be used for this purpose. By transmitting the current location of the mobile device 102 (based on an output from the GPS receiver) to the server system 104, the server system 104 will have information pertaining to the current location of caregivers in the field, assuming each caregiver has an associated mobile device 102.

To provide the home office with information for tracking caregivers, GPS position updates could be periodic, such as every 10 seconds, or based on change in location, such as whenever the GPS coordinates indicate a change in location of more than one kilometer, for example. Other location updating schemes could also be used and are intended to be within the scope of the present invention. In a preferred embodiment, the location-updating period may depend on the schedule maintained by the scheduling module 204, so that if a caregiver is at lunch or on vacation, no GPS updates are transmitted.

An advantage of tracking location of mobile caregivers is that actual driving mileage can be obtained from the transmitted location information. This can help to lessen or eliminate the need for caregivers to manually record their mileage and can help to reduce mileage reimbursement costs for a home care entity. According to one embodiment, the system 100 can also determine a shortest path by including an application on the server computer 114 that can access a map database (such as one produced by NAVTEQ or Tele Atlas NV) that associates roads and other geographic features with coordinates, such as the latitude-longitude information included in a GPS signal. By utilizing known routing software to find a shortest path between an origin and a destination, the server computer 114 can determine the shortest path and compare it, if desired, to the path taken by the caregiver.

Another advantage provided by tracking caregiver location is the ability to identify potential problems, such as when a caregiver is likely to be late for a scheduled visit, based on the current location of the caregiver (as determined from the location of the mobile device 102), the distance to the patient's location, and possibly other information, such as the average or maximum posted speeds for the roads on the shortest path and/or traffic information, from a traffic provider, such as Traffic.com or others. Another exception that can be identified by tracking caregiver location is detecting that a scheduled event never occurred, such as due to the caregiver forgetting or misreading a schedule, for example. This can, in turn, improve customer service should the patient contact the home office regarding the missed visit.

In an alternative embodiment, GPS functionality is partly or completely replaced and/or supplemented by RFID (Radio Frequency Identification) technology for tracking a caregiver's location. This may be particularly useful in a location such as a nursing home or assisted living center, where one or more RFID receivers can be located throughout a facility to track caregivers wearing or carrying coded RFID transmitters. The RFID receivers can then transmit caregiver location and time information to the server system 104 for tracking purposes. Other RFID implementations are also possible, such as RFID triangulation techniques using several RFID receivers for more precise positioning.

Finally, the GPS and travel management module 208 can help home care staff plan optimized patient visit times depending on the optimized route planning. For example, a home care administrator may need to plan a caregiver schedule for five patient visits during a particular day. The GPS and travel management module 208 can intelligently calculate the most economic visit sequence based on a combination of factors including, without limitation, patient location, visit duration, pre-scheduled patients, visit starting location (staff home or home care office), visit ending location (staff home or home care office), and places required to be visited during the day (e.g. physician office or laboratory). In this embodiment, the GPS tracking and travel management module preferably integrates with the workforce management system described above, with respect to the point-of-care caregiver scheduling module.

Clinical Messaging and Notification Module

The clinical messaging and notification module 210 allows for real-time asynchronous communications, as broadcasts, multicasts, or unicasts, depending on the nature of the message to be delivered and its intended recipient list. While typically these may be initiated from the home office for announcements and other purposes, they may also be initiated from a caregiver's mobile device 102, then related to others via the server system 104. An SMS text message delivered to a cell phone is one example of how messaging may be made from the server system 104 to the mobile device 102.

An example of how the clinical messaging and notification module 210 might be used is if there were an epidemic, in which it suddenly became critical to notify all caregivers immediately of the situation so that appropriate action and precautions could be taken. Another example is a simple notification that paychecks are ready for pickup at the home office.

Surgical and Wound Care Management Module

The surgical and wound care management module 212 allows patient surgical and wound conditions to be captured as clinical images for remote clinical observation. These images can be transmitted in real-time from the filed to the home office and/or from aides to skilled nurses to ensure that appropriate assessment and care are provided to the patient.

The clinical images may be captured by a camera or video camera in the mobile device 102. Alternatively, the images may be captured by a separate device (such as a digital camera) and transferred to the mobile device 102, such as via a Bluetooth connection or via a physical memory card transfer. In some embodiments, the caregiver in the field provides a voice annotation that can be associated with the image data, such as to indicate the anatomical location of the images or other observations, such as unexpected odors, etc.

The surgical and wound care management module 212 addresses a possible shortcoming that faces the home care industry—the relative lack of patient observation by a skilled practitioner as compared to an in-patient. Of the approximately 42 million people that undergo surgical operations in the United States each year, approximately 40% of the procedures are accompanied by post-operative complications, such as infections, thrombo-embolic events, respiratory complications, and adverse cardiac outcomes. The surgical and wound care management module 212 provides a mechanism for providing clinical observation without the negative consequences associated with a prolonged hospital stay.

Supply Order Fulfillment Module

The supply order fulfillment module 214 addresses a common inefficiency observed in typical, traditional home care practices—ordering supplies needed in the field. This module enables a mobile caregiver to place supply order requests from his or her mobile device 102 at the point of need (the patient's home or other location). The supply order requests are transmitted to the server system 104, where they can be aggregated at an application on the server computer 114 for order fulfillment.

Disease Management Intelligence Module

The disease management intelligence module 216 can provide caregivers with information and reminders regarding their patients' health conditions, which may be particularly useful in post-discharge settings. The server system 104 can maintain a database of clinical contents and rules, then send out messages and/or alerts (e.g. through SMS messages to the mobile device 102), based on data sent by the caregiver from the mobile device 102 to the server system 104. For example, a caregiver, upon transmitting a patient's heart rate from the mobile device 102 to the server system 104, might receive a message from the disease management intelligence module 216 on the server computer 114 indicating that the measured heart rate is higher than a predetermined threshold and that the caregiver should remind the patient to take a recommended dosage of a prescribed medicine, in order to assist in reducing the patient's heart rate. Generally, the disease management intelligence module 216 is an application on the server computer 114 that applies a set of clinical contents and rules to data received from the caregiver and transmits alerts and or recommendations if the received data meets an alert condition. In a preferred embodiment, the clinical contents and rules are abstracted from one or more evidence-based medical resources. Alternatively, the clinical contents and rules may be manually entered, such as by a home office staff person or health care professional.

Administrative Center Module

The administrative center module 218 is preferably a portal on the server computer 114 that allows home care administrators and office staff to manage a home care business operating the home care administration system 100. In a preferred embodiment, the portal is a web-based portal offering anytime/anywhere information access, to that the business can be managed virtually. This promotes telecommuting and will generally tend to reduce timelines associated with scheduling, approving, and submitting invoices for payment. This, in turn, can shorten accounts-receivables timelines, which will typically be a financial benefit for the home care business. While the system 100 is pictured as having a single server computer 114 to act as a web portal, there may instead be multiple server computers 114 at a single location (for load balancing and redundancy, for example), or there may alternatively be different server computers 114 affiliated with regional or local home care offices and having different web addresses from one another.

One function support by the administrative center module 218 is managing users of the system 100. A home care administrator and/or office staff person can add, delete, and/or edit users of the system, such as caregivers and others. In addition, other properties associated with each user may be defined, such as roles, permission levels, and authority hierarchies, for example. The administrative center module 218 residing on the server computer 114 provides for numerous roles that assign different rights to users communicating with the server computer 114.

A second function relates to tasks that may be performed by a caregiver for a particular function. While the electronic visit record and care plan module 206 is the primary module for defining a care plan comprised of tasks, the administrative center module 218 can serve as the interface for selecting, defining, and modifying tasks to be performed. Correspondence between tasks in the system 100 and tasks supported by outside reimbursement agencies (e.g. Medicare) can also be determined at the administrative center module 218.

Another function of the administrative center module 218 is to manage visits. In a preferred embodiment of the invention, six visit types are defined: scheduled visit, open visit, pending visit, approved visit, denied visit, and archived visit. Each of these will now be summarized in turn. Additional details are set forth with respect to FIG. 3 and its accompanying description.

A scheduled visit is a visit that has a care plan associated with it and that has been scheduled to be performed by a caregiver. An office administrator (admin) or an appropriate delegate may be responsible for setting the daily tasks for the caregiver. This includes creating, reviewing, and editing task lists that the caregiver is to perform during a visit to a patient's home. The admin prepares the patient visits, for example, by using the administrative center module 218 on the server computer 114. After a patient is entered (or already exists) on the server computer 114, the admin creates or edits an individualized patient task list by checking which tasks an agent is to perform during a visit. The admin saves patient information for storage at the server computer 114. In one example, the admin adds or edits patient information for database storage associated with the server computer 114. Information such as the patient's name, address, latitude-longitude information, patient medical record number(s), location (servicing home-care office), and a corresponding task list may be entered manually. Alternatively, the administrative center module 218 provides a method to import patient information using one or more techniques (discussed in further detail with respect to FIG. 3). After the appropriate patient information is entered in the administrative center module 218, the admin creates or edits a patient task list by checking which tasks an agent is to perform during one or more visits. The admin saves the patient information for storage in memory.

An open visit is a visit that is being performed by a caregiver or other person in the field. Visits can thus be monitored as they happen. Caregivers perform visits using the mobile devices 102. The admin is able to view visits that have been started by a caregiver in real time. The visit can also be deleted should the visit be abandoned accidentally. The server computer 114 can display a visit in at least four different views, according to one embodiment: open, pending, approved, and history. When a visit is in the open state an application on the server computer 114 will query a database, such as a MySQL database, for all appropriate open visits, such as open visits tied to the location to which the admin account is linked in a customer_accounts table. The resulting visits list is displayed on the server computer 114 under an "open visits" field. If the role assigned to the admin account has all "open visit" permissions then the admin account will be able to delete, complete, or view that open visit. A "delete visit" function will completely remove the visit and related visit tasks from the database. A "complete open visit" function will update the visit status from "open" to "pending". A "view visit" function will display the visit information that includes the visit tasks.

A pending visit is a visit that has been completed by a caregiver (or other person in the field) that has not yet been "approved." When a caregiver completes a visit, the admin is able to view the caregiver's finished visit in the "pending visit" section of the administrative center module 218. The admin can also edit the pending visit to ensure completeness of visit information. This allows the admin to ensure all visit data is correct, and also allows the admin to make corrections. This ensures that the visit meets compliance. The visit can also be deleted should the visit not meet completeness or compliance. This allows the agent to be re-scheduled, if desired. When a visit is in the "pending" state, the administrative center module 218 will query a database, such as the MySQL database described above, for all pending visits tied to the admin's location, such as the location to which the admin account is linked in the customer_accounts table described above. The resulting visits list will be displayed on the server computer 114 under "pending visits." If the role assigned to the admin account has all pending visit permissions then the admin will be able to delete, move to "approved," view, or move-all to "approved." The "delete visit" function will completely remove the visit and related visit tasks from the database. The "move to approved visit" function will update a single visit's status from "pending" to "approved." The "view visit" function will display the visit information that includes the visit tasks, in an html form (or another convenient format) that enables the admin to make changes to the visit information to ensure data integrity. The "move all to approved" function allows the admin to move all "pending" visits and allows the admin to update the status of all the listed visits to "approved" status.

An approved visit is a visit that has approved by the admin. The admin is able to determine if a visit is completed properly using the "pending visit" functionality described above. In the presently described embodiment, once the admin moves a visit to "approved visit" status, that visit can no longer be edited or deleted.

A denied visit is a visit that has been denied by the admin. The admin is able to determine if a visit has not been completed properly using the "pending visit" functionality described above. In the presently described embodiment, when the admin moves a visit to "denied visit" status, that visit can be edited for accuracy and completeness and then moved to "approved visit" status, if appropriate.

An archived visit is a visit that has previously been approved and is to be saved for record-keeping purposes. The admin selects visits in the "visit approved" section for archiving. The admin may select individual visits, all visits, or a subset of all visits. Once a visit is moved to "archive," that visit is no longer active. The "move to archive" function places the visit into a holding area, where the visit information can be exported manually through the administrative center module 218, or automatically via the methods mentioned in reference to FIG. 3. Visit information preferably remains in an archived state within the administrative center module 218 indefinitely. This allows for future reporting on all visit information.

Enterprise Application Integration Module

The enterprise application integration module 220 may be included in the system 100 if the system 100 will be integrated with applications from third parties. The enterprise application integration module 220 includes application components that are designed to communicate with other home care systems and has features to support multiple communication protocols, including, without limitation, HTTP, FTP, and Secure FTP. Possible data structures that may be embodied in such communication protocols include HL7, XML, CSV, and other formats. The module is flexible to support real-time communication and file batch communication. The enterprise application integration module 220 also includes a data mapping utility that maps incoming data messages from the third party format into its own data format that the database server 120 supports.

For example, the billing/accounting system 122 shown in FIG. 1 may be a third-party application. The enterprise application integration module 220 would allow that third-party application to integrate and interoperate with applications on the server computer 114 and/or the database server 120, for example. This may enable administrators and/or other home office staff to view integrated and complementary views of financial and billing information. Other third-party applications that might be partly or entirely integrated into the system 100 using the enterprise application integration module 220 are a scheduling and/or payroll system, a clinical medicine database application, Medicare compliance applications, and others. The information exchanged between the enterprise application integration module 220 and third-party applications may be exchanged in real-time or near real-time, for example.

Figure 2A:
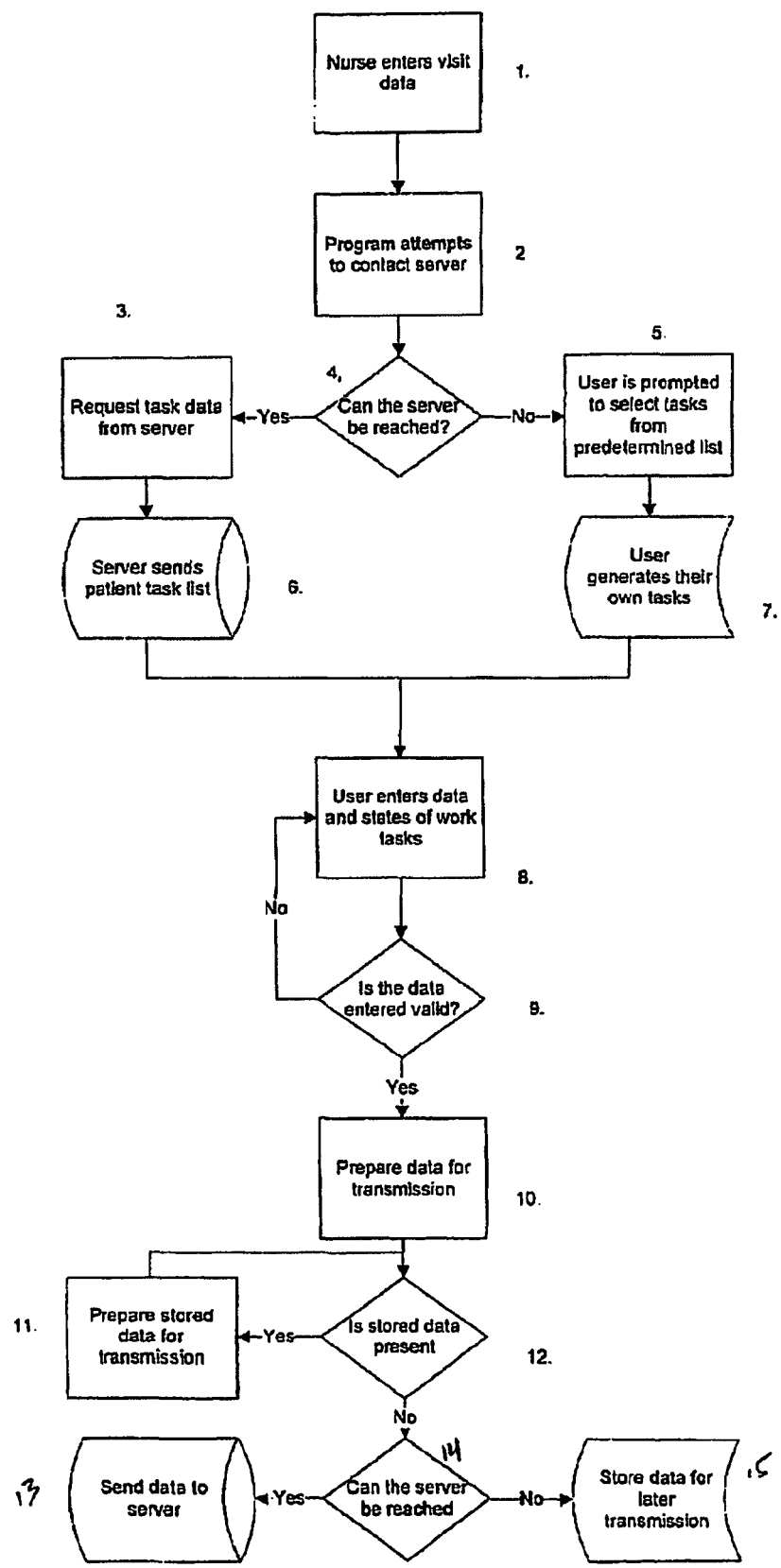
FIG. 2a is a flow chart illustrating the steps associated with initiating and establishing bi-directional communication with the communication device and remote server system.

Referring to FIG. 2a, steps related to the application programming associated with the mobile device 102 are provided and shown, according to a preferred embodiment. Part of the processing related to the system 100 is software which is targeted to mobile devices 102 (i.e., the "client"). When an agent, such as a caregiver, enters a home, the agent launches this specified application, which begins the following process shown in steps 1-15 of FIG. 2a.

In step 1, FIG. 2a, the agent is first prompted to enter characters identifying the agent and patient. With this data, the client software attempts to make contact with the server computer 114, via an HTTP communication protocol in step 2, FIG. 2a. Upon successful communication between the client mobile device 102 and server computer 114 in step 4, the server computer 114 is able to provide the client mobile device 102 with the tasks that are associated with the patient. This indicates the creation of a "visit," along with tasks that are associated. In step 3, the client mobile device 102 requests task data from the server computer 114. The server computer 114 then provides this information to the client mobile device 102, via an HTTP response as seen in step 6, FIG. 2a.

If communication cannot be established between the server computer 114 and client mobile device 102 as seen in step 4, the client mobile device 102 falls into a failsafe mode, which prompts the user to select which tasks he or she is to perform with this patient from a predetermined list, step 5, FIG. 2a. Once the agent has a selection of tasks that are generated by the user/agent (step 7, FIG. 2a), the client mobile device 102 then allows the agent to report the states of these tasks. The "states" are indicators of the outcome of performance for the task. Examples include, but are not limited to: the task was completed as required, the patient refused to have the task performed, etc. These task states might have data associated with them. Examples would be a numerical number to indicate: the patient's temperature, the patient's pulse rate, etc. The application on the client mobile device 102 provides an interface which collects this data from in the user/agent as seen in step 8, FIG. 2a.

When the agent has finished entering required data at step 9, FIG. 2a, the client application then performs a series of validations on the data, to make certain that the state of each task has been reported. Once the data has been verified to be correct, the application on the client mobile device 102 prepares the data for transmission, in step 10, FIG. 2a. If the data is stored, in step 11, the stored data is prepared for transmission. In step 12, FIG. 2*a*, a determination is made as to whether stored data is present. If it is, processing proceeds to step 11. If the stored data is not present, then the processing moves to step 14, FIG. 2*a*, to determine if the server computer 114 can be reached. If a contact attempt is successful, the client mobile device 102 transmits the data to the server computer 114, which is recorded and stored at the server system 104, such as at the database server 120, as seen in step 13, FIG. 2*a*.

If however the contact attempt fails to reach the server computer 114 in step 14, the application on the mobile device 102 will store the data associated with the visit onto the data repository of the mobile device 102, as shown in step 15, FIG. 2*a*. This data will be held until such time that the mobile device 102 makes a successful connection with the server computer 114 with a future visit. If the application on the mobile device 102 detects that it has stored data from previous failed transmissions, this data is prepared for transmission on each subsequent data transmission attempt as seen in step 10, FIG. 2*a*.

Figure 3:
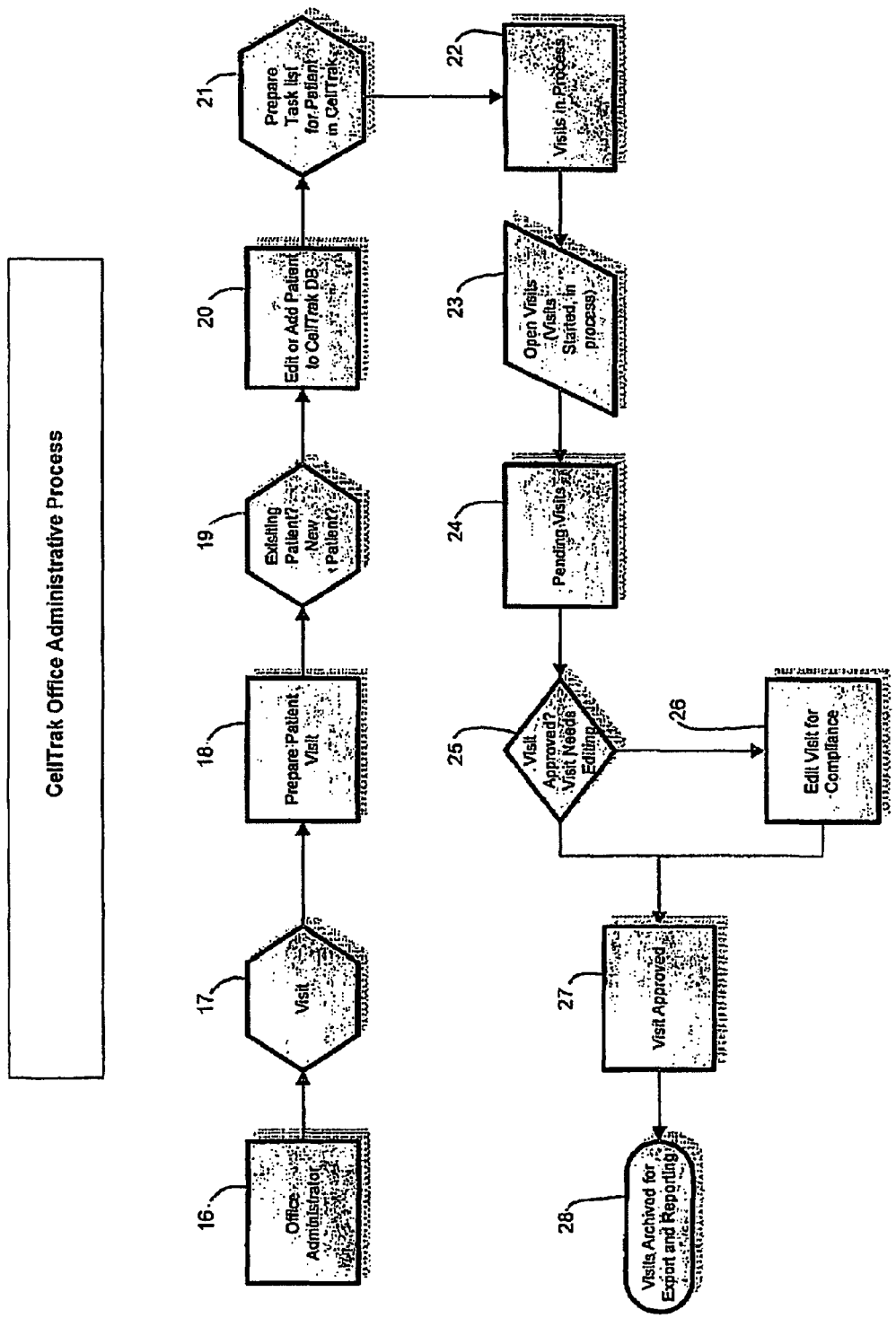
FIG. 3 is a flow chart illustrating the steps associated with an office administrative process as part of the home care administration system.

Referring now to FIG. 3, a flowchart diagram illustrating steps performed in association with a web portal server computer 114 of the server system 104 is shown. In block 16, FIG. 3, an office administrator (admin) refers to employees at the local office (Location) level, responsible for setting the daily tasks for the field personnel agent (such as a home healthcare service staff member or caregiver). This includes creating, reviewing and editing task lists that the agent is to perform during a visit to the home of the patient(s). Visits are monitored as they happen (Open Visits). This further entails reviewing and editing, if necessary, visits that have been completed by the agent (Pending Visits) and approving visits (Approved Visit). The web application residing on the server computer 114 provides for numerous roles that assign different rights to users communicating with the server computer 114. The admin also has the responsibility of adding other office users into the web portal computer application and assigning these roles to the appropriate users.

In block 17, FIG. 3, "visit" is terminology used in the web portal computer application to describe the activity of an agent operating a mobile device 102 in the field. The agent, for example, is responsible for visiting patients in their homes, nursing homes, hospitals, or wherever a patient may be located. The web portal computer application tracks these visits through the entire visit cycle as the communication device of the agent is used.

In block 18, FIG. 3, the admin prepares for patient visits using the web portal computer application. In block 19, FIG. 3, the admin checks to see if information exists in the web portal computer application. After a patient is entered in the web portal computer application, in block 20, FIG. 3, the admin creates or edits a patient task list by checking which tasks an agent is to perform during a visit. The admin saves patient information for storage at the web portal computer.

In one example, the admin adds or edits patient information for database storage associated with the web portal computer. The web portal computer application provides a method to enter patient information manually, including, but not limited to:
  Patient name
  Patient address
  Latitude and longitude information
  Patient Medical Record Number(s)
  Location (Office responsible for patient)
  Task List(s)

Figure 8:
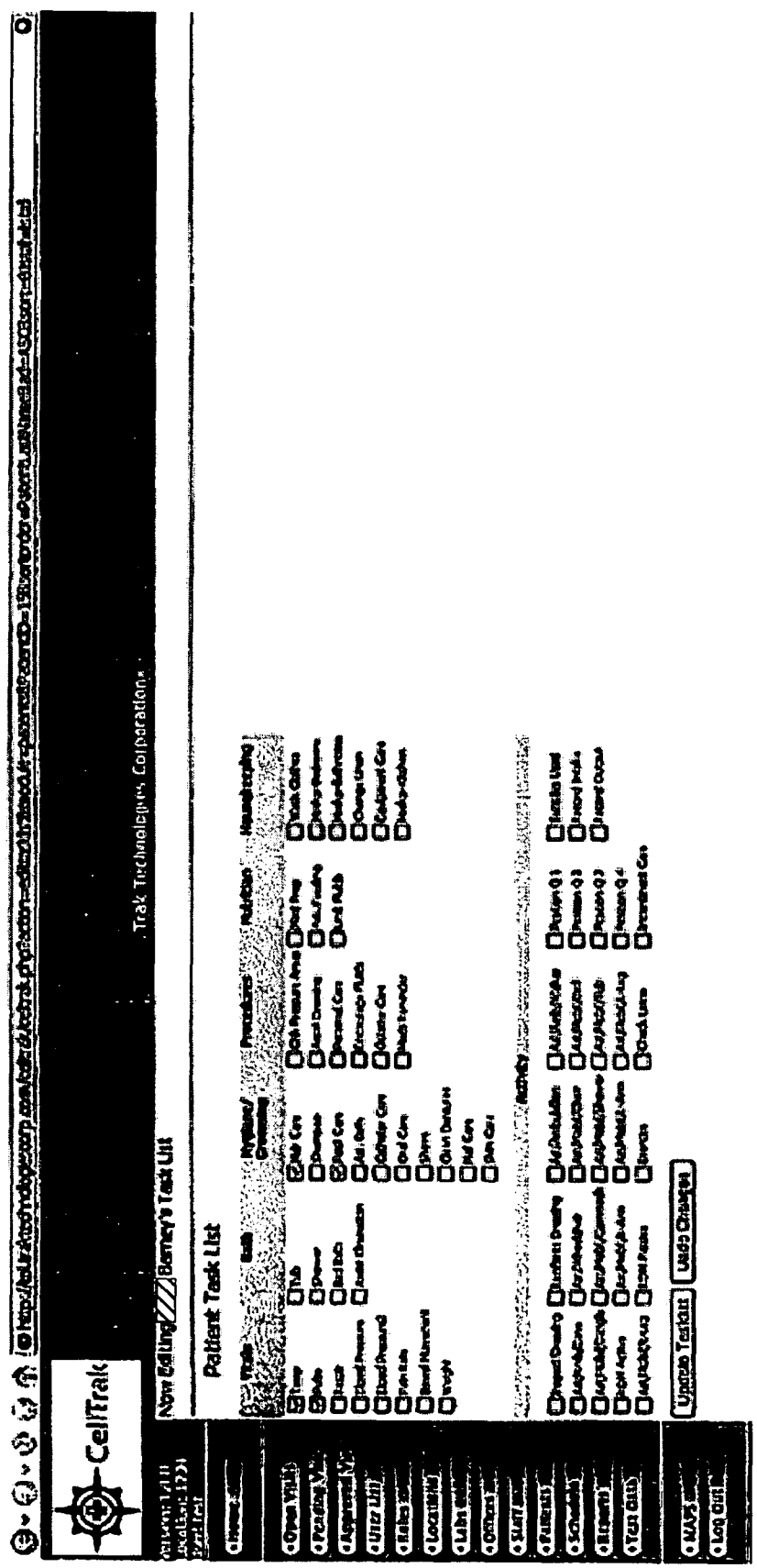
FIG. 8 shows a pictorial representation of a display screen for a web portal server computer, showing a task-list editing application, for designing a patient's care plan, according to one embodiment of the invention.
Figure 9:
FIG. 9 shows a pictorial representation of a display screen for a web portal server computer, showing a patient record editing interface, according to one embodiment of the invention.

(See FIG. 9.) Alternatively, the web portal computer application provides a method to import patient information using the following methods, without limitation:
  Remote via SFTP
  Remote via HTTPS
  Local via TCP/IP
  Formats, csv, xls, dbf, XML, or database connection After the appropriate patient information is entered in the server computer 114, in block 21, FIG. 3, the admin creates or edits a patient task list by checking which tasks an agent is to perform during one or more visits (see FIG. 8). The admin saves the patient information for storage in memory or other data storage, such as the database server 120. In block 22, visits in process take place. The agents perform visits using the mobile devices 102 operating under the software program application as described in FIG. 2*a*.

Block 23 refers to Open Visits. The admin is able to view visits that have been started by an agent in real time. The visit can also be deleted should the visit be abandoned accidentally. The web portal server computer 114 can display a visit in at least four different views: Open, Pending, Approved, and History. When a visit is in the open state the web computer application will query a database for all open visits tied to the location that the admin account is linked to in a customer_accounts table. The resulting visits list is displayed in the server computer 114 under "open visits." If the role assigned to the admin account has all open visit permissions then the admin account will be able to delete, complete, or view that open visit. A "delete visit" function will completely remove the visit and related visit tasks from the database. A "complete open visit" function will update the visit status from "open" to "pending". A "view visit" function will display the visit information that includes the visit tasks.

Block 24, FIG. 3, relates to Pending Visits. When an agent completes a visit, the admin is able to view the agent's finished visit in the Pending Visit section of the web portal computer application. The admin can also edit the pending visit to ensure completeness of visit information. This allows the admin to ensure all visit data is correct, and also allows the admin to make corrections. This ensures that the visit meets compliance. The visit can also be deleted should the visit not meet completeness or compliance. This allows the agent to be re-scheduled. When a visit is in the pending state the web computer application will query the database for all pending visits tied to the location that the admin account is linked to in the customer_accounts table. The resulting visits list will be displayed in the web portal server computer 114 under pending visits. If the role assigned to the admin account has all pending visit permissions then the admin will be able to delete, move to approved, view, or move all to approved. The "delete visit" function will completely remove the visit and related visit tasks from the database. The "move to approved visit" function will update a single visit's status from "pending" to "approved". The "view visit" function will display the visit information that includes the visit tasks, in an html form that enables the admin to make changes to the visit information for data integrity. The "move all to approved" function allows the admin to move all pending visits and will allow the admin to update the status of all the listed visits to "approved" status.

Block 25, FIG. 3, relates to visit approval, so that a determination is made as to whether the visit is approved or needs editing. The admin is able to determine if a visit is completed properly using "Pending Visit". If the Visit is complete, the visit can be moved to next stage. Block 26, FIG. 3, relates to "Edit Visit for Compliance". If the visit is not complete, it can be edited for completeness and then moved to the next stage, "Visit Approved" (block 27). When the admin moves a visit to this stage, the visit can no longer be edited or deleted.

Block 27, FIG. 3, relates to visits approved and visits archived. The admin selects visits in the "visit approved" section for Archiving. The admin may select individual visits, or select all visits. Once a visit is moved to Archive, the visit is no longer active. The "move to Archive" function places the visit into a holding area, where the visit information can be exported manually through the web portal computer application, or automatically via the methods mentioned in relation to block 13. Visit information remains in an archived state within the web portal computer application indefinitely. This allows for future reporting on all visit information.

Block 28, FIG. 3, relates to visits archived for export and reporting. When a visit is in the approved state, the web application will query the database for all approved visits tied to the location that the admin account is linked to in the customer_accounts table. The resulting visits list will be displayed in the web portal under "approved visits". If the role assigned to the admin account has all approved visit permissions, then the admin account will be able to move all to history, move to history, or view approved visits. The "move all to history" function will move the database entry from the "visits" table to the "history visits" table and it will move the visit tasks from the "tasks" table to the "history tasks" table for all approved visits displayed. The "view visit" function will display the visit information and all related tasks with status. The "move to history" function will move the database entry from the "visits" table to the "history visits" table and it will move the visit tasks from the "tasks" table to the "history tasks" table for the selected visit only.

Figure 4:
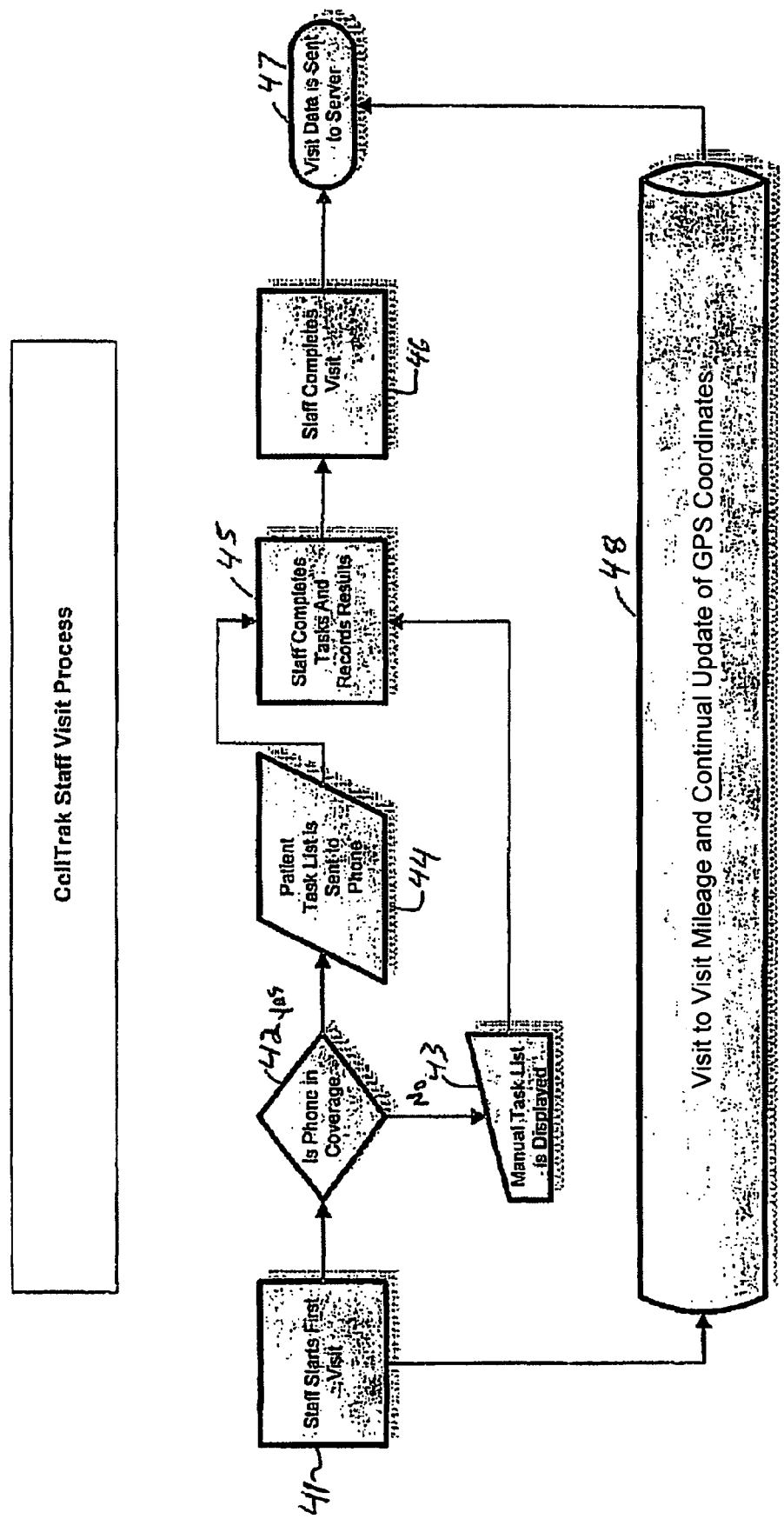
FIG. 4 is a flow chart illustrating the steps of a field personnel visitation process associated with a communication device and related tracking as part of the home care administration system.

Referring to FIG. 4, the steps related to a field service agent (e.g. a caregiver) using the mobile device 102 during the process of a field visit, according to one embodiment, are shown. In block 41 the field service agent interacts with the mobile device 102 and initiates a first visit component associated with the software-based client application of the mobile device 102. In block 42, FIG. 4, it is determined if the mobile device 102 is in coverage for telephonic and/or data communication. If the mobile device 102 is not in coverage, then in block 43, a manual task list is displayed listing the tasks to be accomplished by the field agent using the mobile device 102. Processing then proceeds to block 45, in which the field service agent completes tasks and records results.

If the mobile device 102 is in coverage, then in block 44, FIG. 4, a patient task list is transmitted from the server system 104 to the mobile device 102 operated by the agent in the field. In block 45, the field service agent completes tasks and records results. In block 46, the field service agent completes the visit and in block 47 the visit data gathered and obtained is transmitted by mobile device 102 for receipt by the server computer 114 of the server system 104. Throughout this process, in block 48, the GPS application records visit-to-visit mileage and continues to provide updates of the GPS coordinates of the location of the mobile device 102 to the server system 104.

Figure 5:
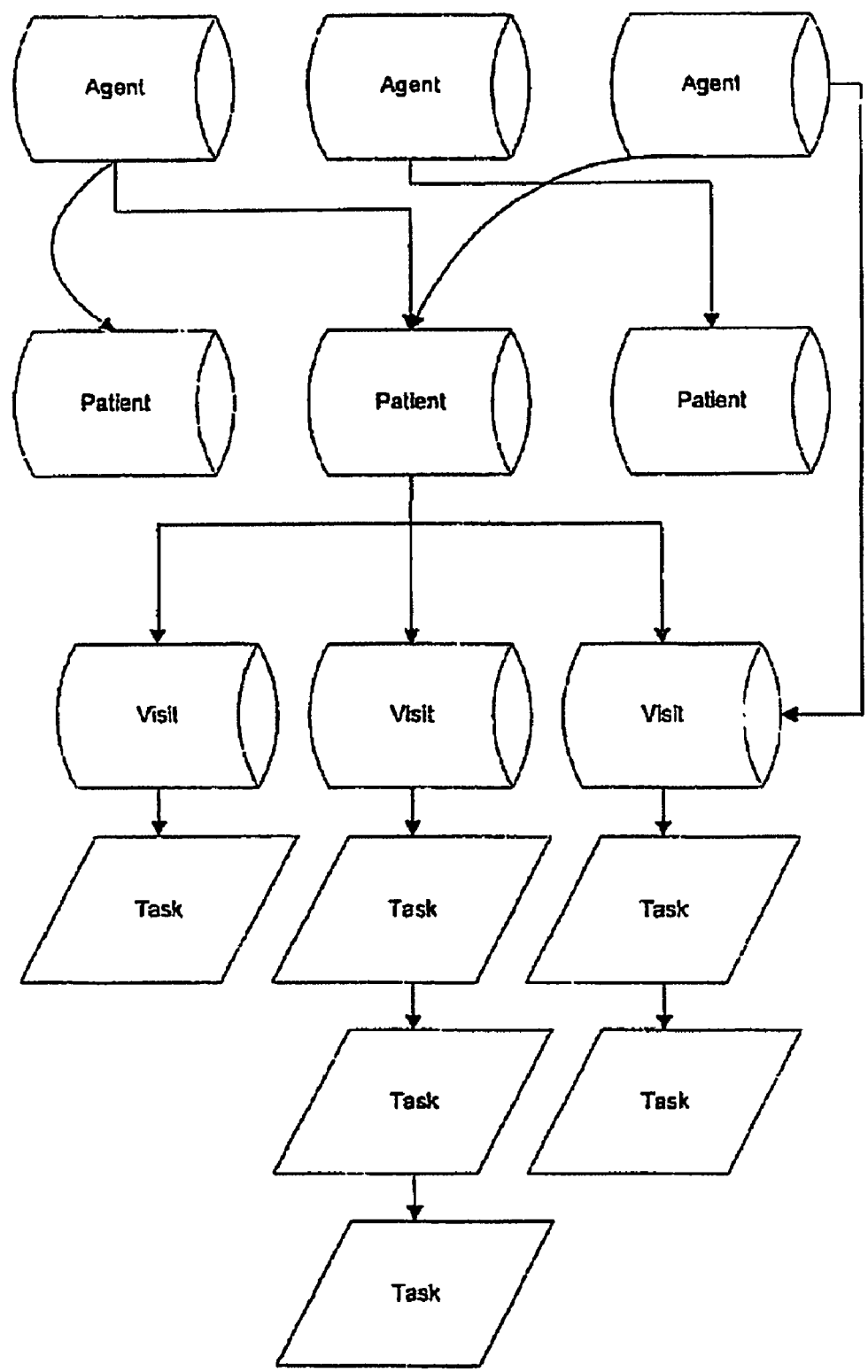
FIG. 5 is an illustrative diagram representing relationships between communication device field service users/agents, patients, visits by field service users/agents and tasks performed.

As seen in FIG. 5, a representation model illustrating an example of relationships between the agents using the mobile devices 102, the patients, and the visits and tasks performed is shown. An "agent" refers to a user. For the purposes herein, this user may be the field personnel staff member (e.g. caregiver) which goes to a particular patient to perform tasks. A "patient" may refer to an individual that the agent will service.

A "task" is a duty that is to be performed on a patient. Examples of tasks could be, but not limited to: taking a patient's temperature, recording the date of the patient's last bowel movement, washing the patient's hair, etc. There is therefore, a one-to-many relationship between patients and tasks. Each patient might have several, if not dozens of tasks that can be assigned to them. A "visit" may refer to a particular instance of an agent performing a set of tasks. A visit preferably has a one-to-one relationship with a patient. A visit may selectively only correspond to one patient. Note, however, that one patient might have several visits associated with them (i.e. the relationship between patients and visits is one-to-many) as seen in FIG. 5.

FIGS. 6A-19 illustrates representative screen shots for the applications and modules described above for the mobile device 102 and the server system 104. These screen shots are merely examples, and other alternative implementations are also intended to be included within the scope of various embodiments of the invention.

FIG. 6A shows pictorial representations of a display screen for a mobile device 102, showing an initialization procedure, according to one embodiment of the invention.

FIG. 6B shows pictorial representations of a display screen for a mobile device 102, showing data inputs to complete tasks and a conclusion procedure, according to one embodiment of the invention.

FIG. 6C shows a pictorial representation of a display screen for a web portal server computer 114, showing a map-based tracking application, according to one embodiment of the invention.

Figure 7:
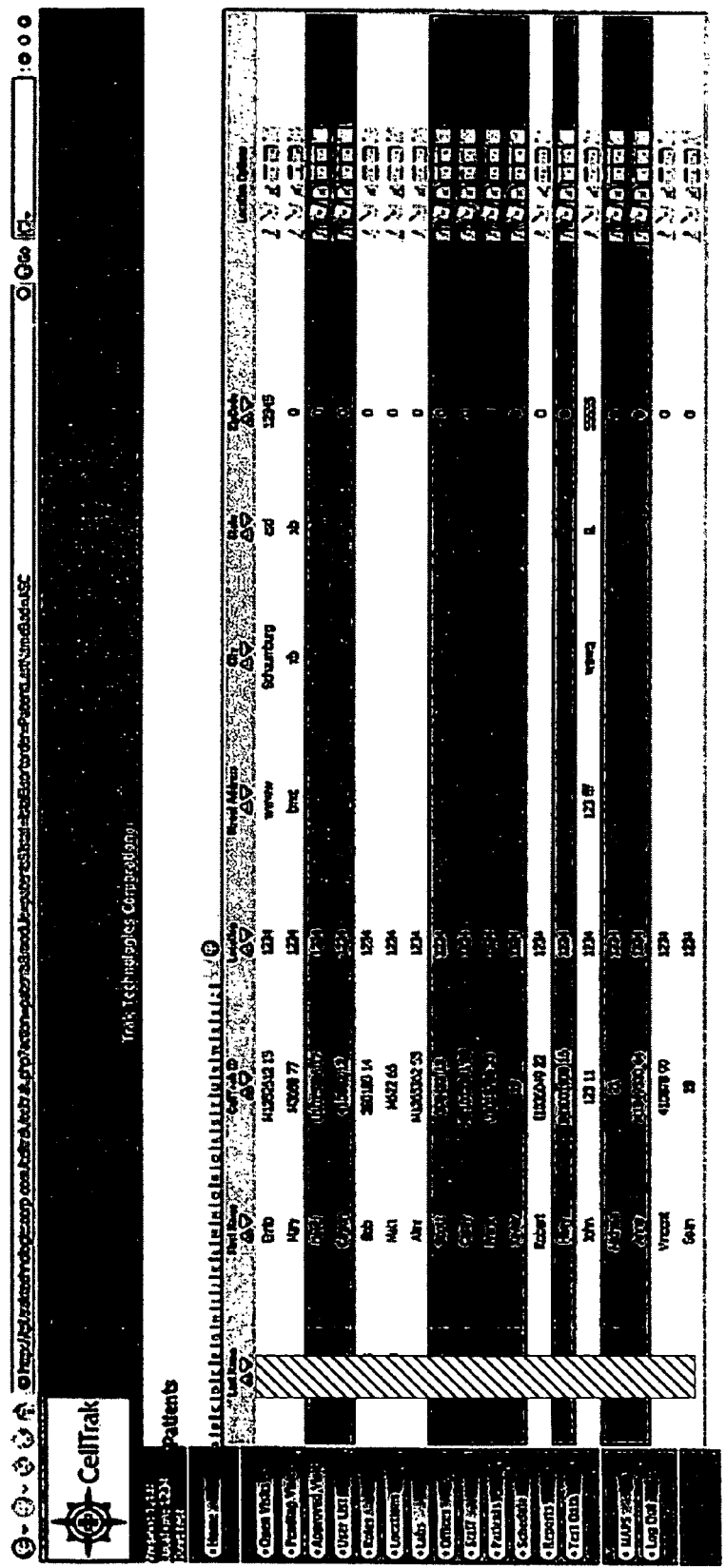
FIG. 7 shows a pictorial representation of a display screen for a web portal server computer, showing a patient database, according to one embodiment of the invention.

FIG. 7 shows a pictorial representation of a display screen for a web portal server computer 114, showing a patient database, according to one embodiment of the invention.

FIG. 8 shows a pictorial representation of a display screen for a web portal server computer 114, showing a task-list editing application, for designing a patient's care plan, according to one embodiment of the invention.

FIG. 9 shows a pictorial representation of a display screen for a web portal server computer 114, showing a patient record editing interface, according to one embodiment of the invention.

Figure 10:
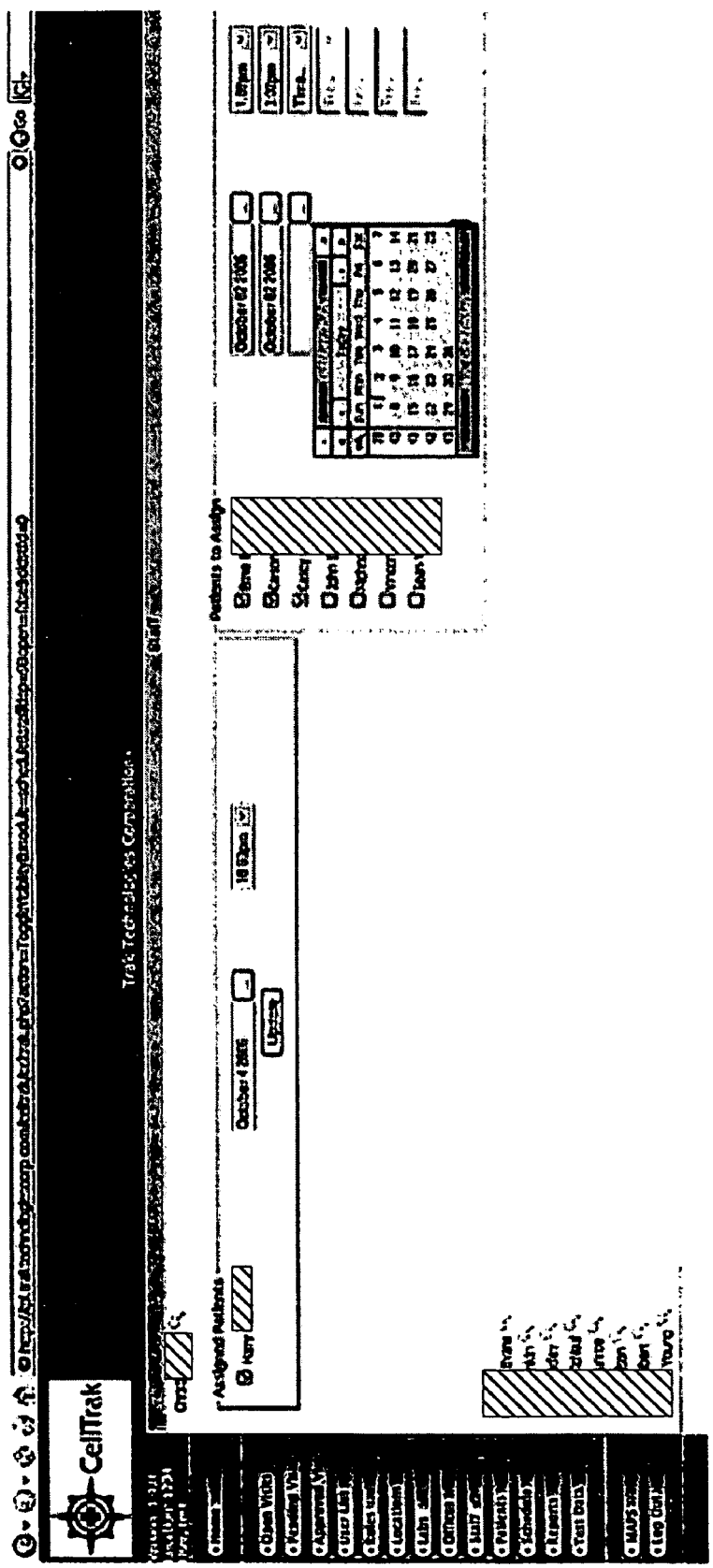
FIG. 10 shows a pictorial representation of a display screen for a web portal server computer, showing a staff scheduling application, according to one embodiment of the invention.

FIG. 10 shows a pictorial representation of a display screen for a web portal server computer 114, showing a staff scheduling application, according to one embodiment of the invention.

Figure 11:
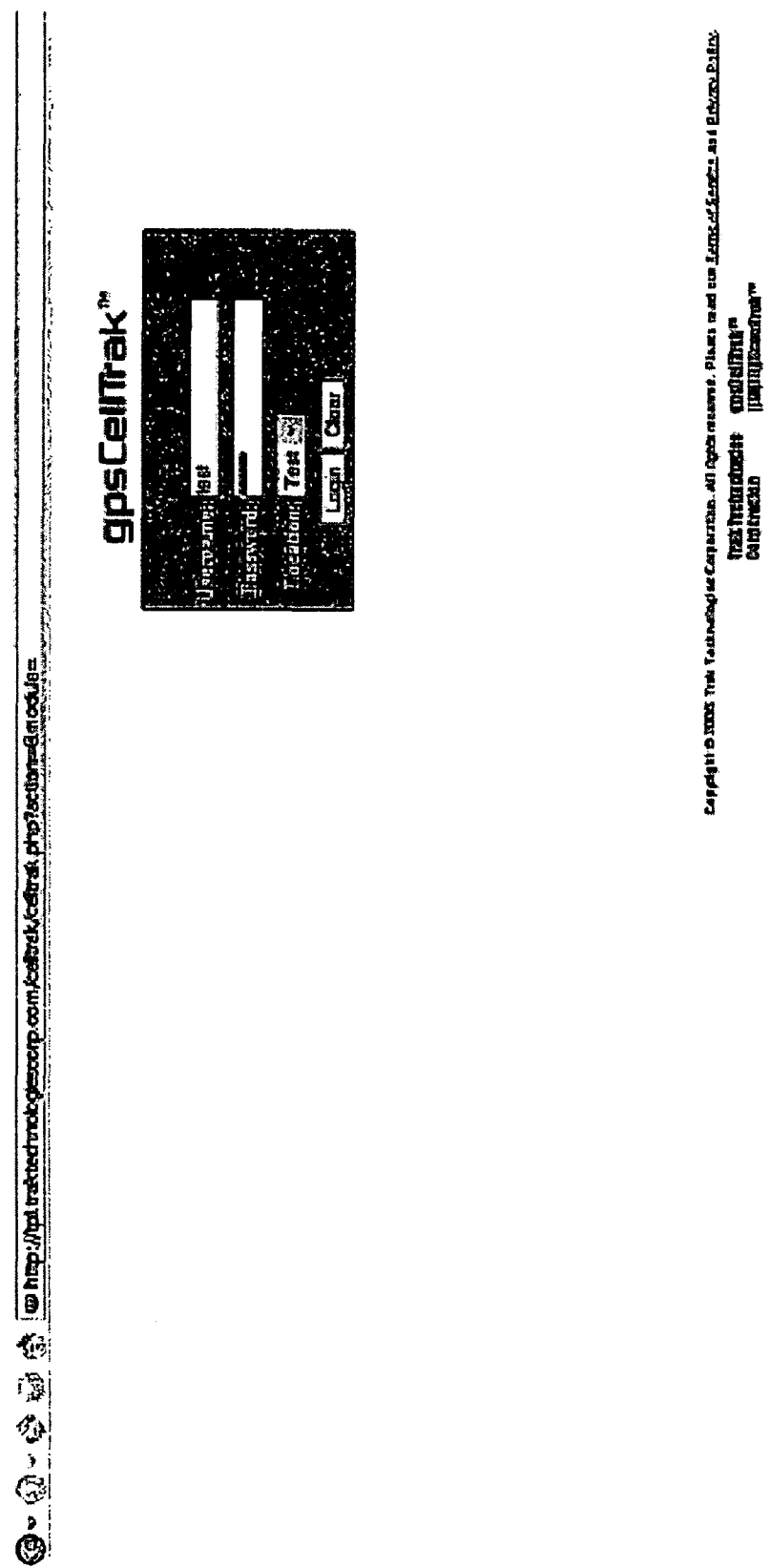
FIG. 11 shows a pictorial representation of a display screen for a web portal server computer, showing a login screen according to one embodiment of the invention.

FIG. 11 shows a pictorial representation of a display screen for a web portal server computer 114, showing a login screen according to one embodiment of the invention.

Figure 12:
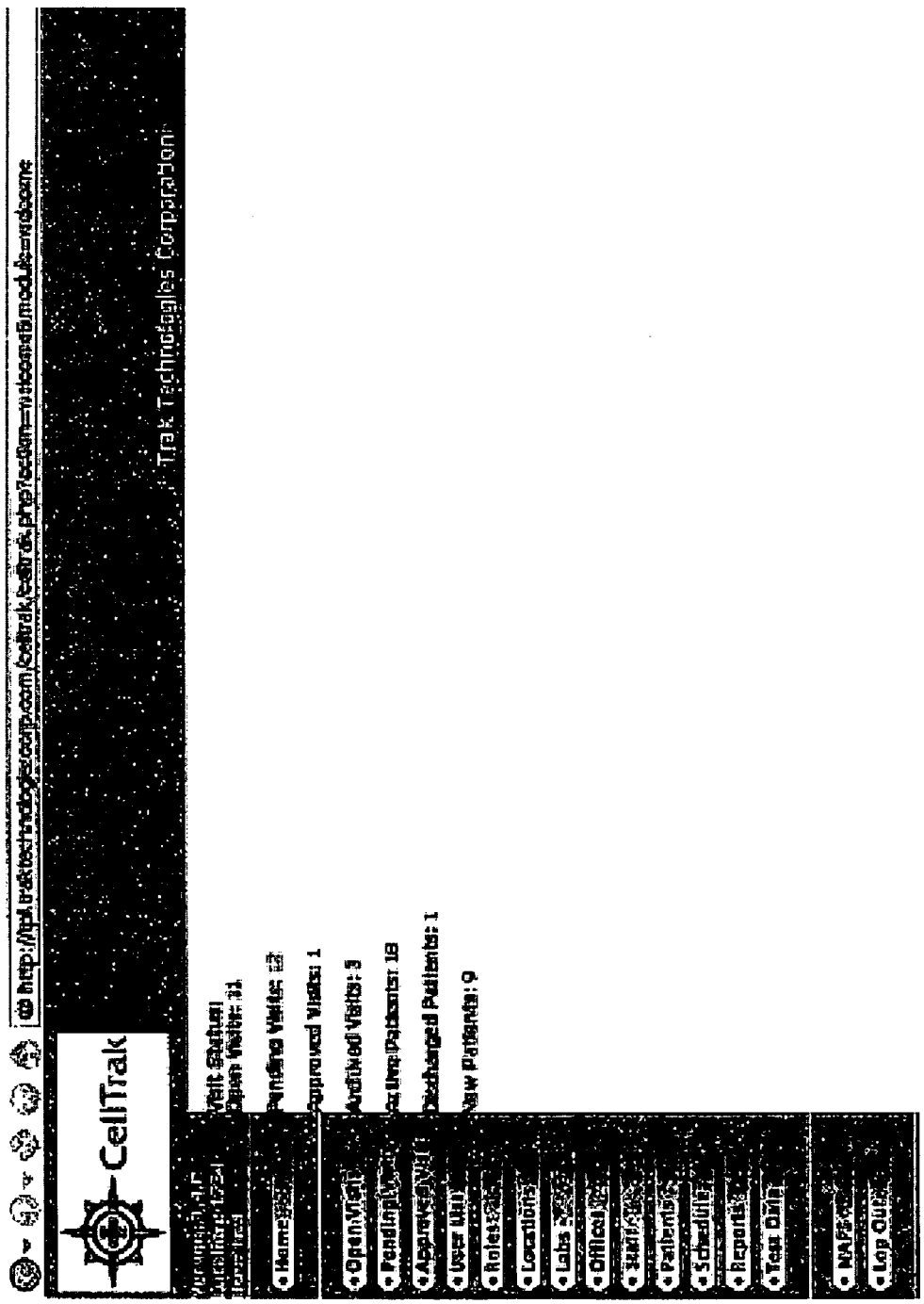
FIG. 12 shows a pictorial representation of a display screen for a web portal server computer, showing a visit status summer screen, according to one embodiment of the invention.

FIG. 12 shows a pictorial representation of a display screen for a web portal server computer 114, showing a visit status summer screen, according to one embodiment of the invention.

Figure 13:
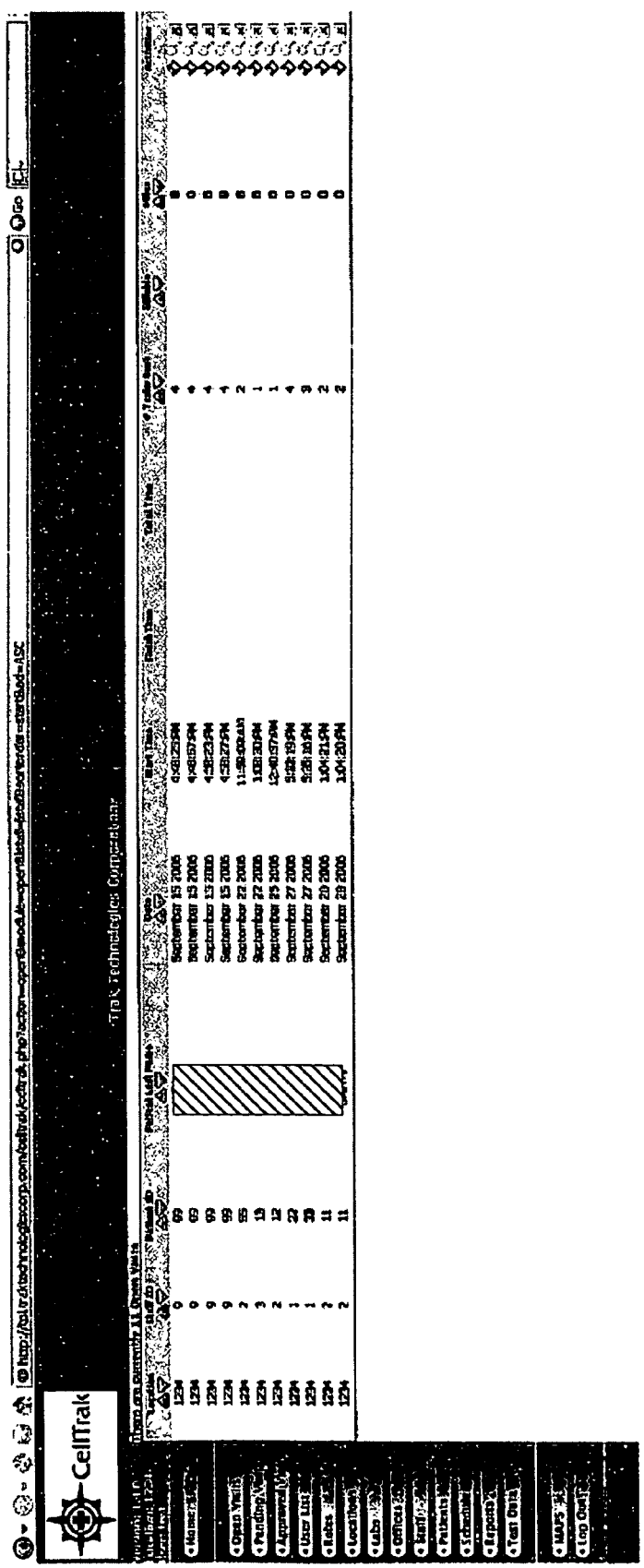
FIG. 13 shows a pictorial representation of a display screen for a web portal server computer, showing an "open visits" summary screen, according to one embodiment of the invention.

FIG. 13 shows a pictorial representation of a display screen for a web portal server computer 114, showing an "open visits" summary screen, according to one embodiment of the invention.

Figure 14:
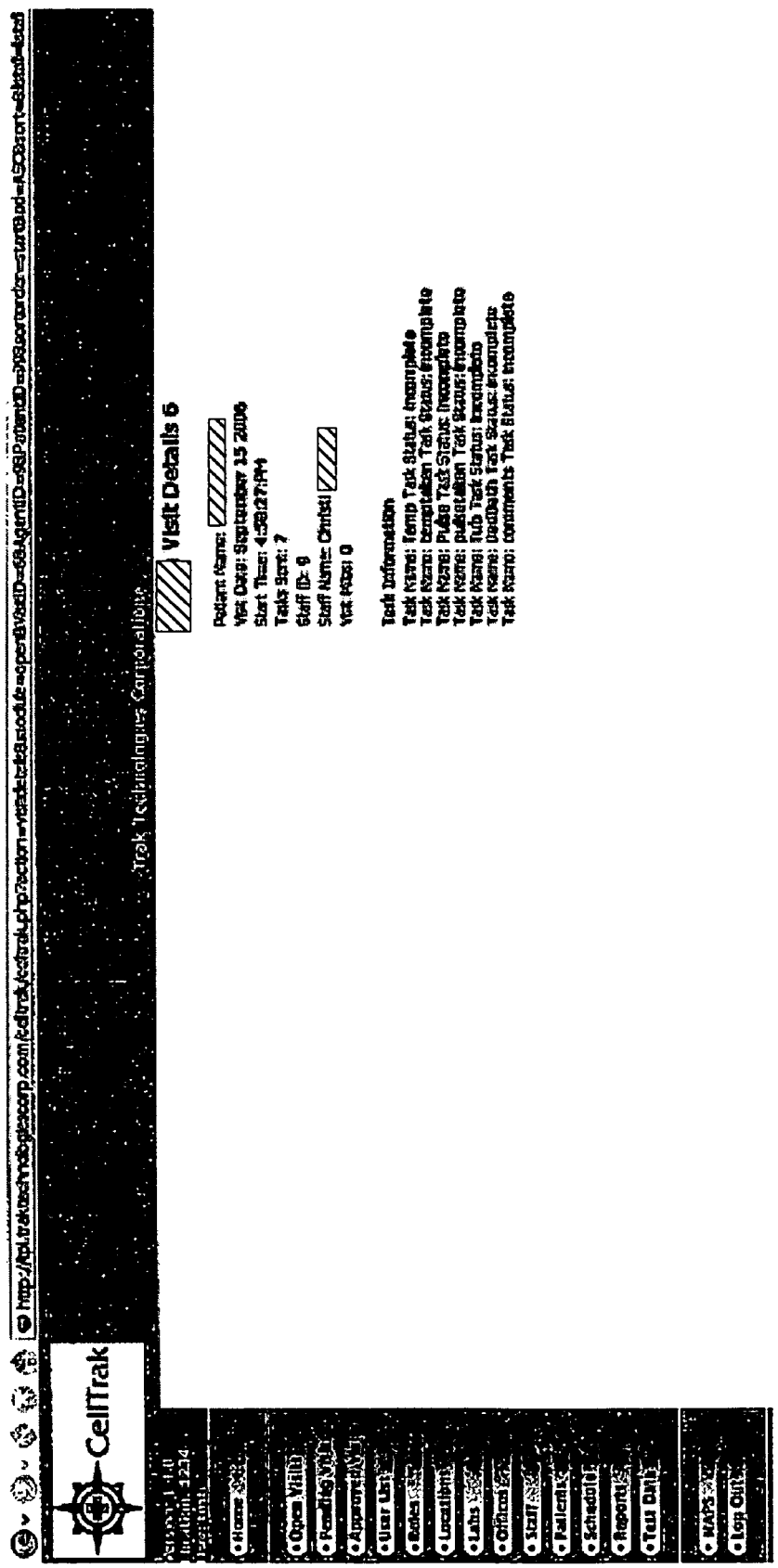
FIG. 14 shows a pictorial representation of a display screen for a web portal server computer, showing an "open visit" details screen, according to one embodiment of the invention.

FIG. 14 shows a pictorial representation of a display screen for a web portal server computer 114, showing an "open visit" details screen, according to one embodiment of the invention.

Figure 15:
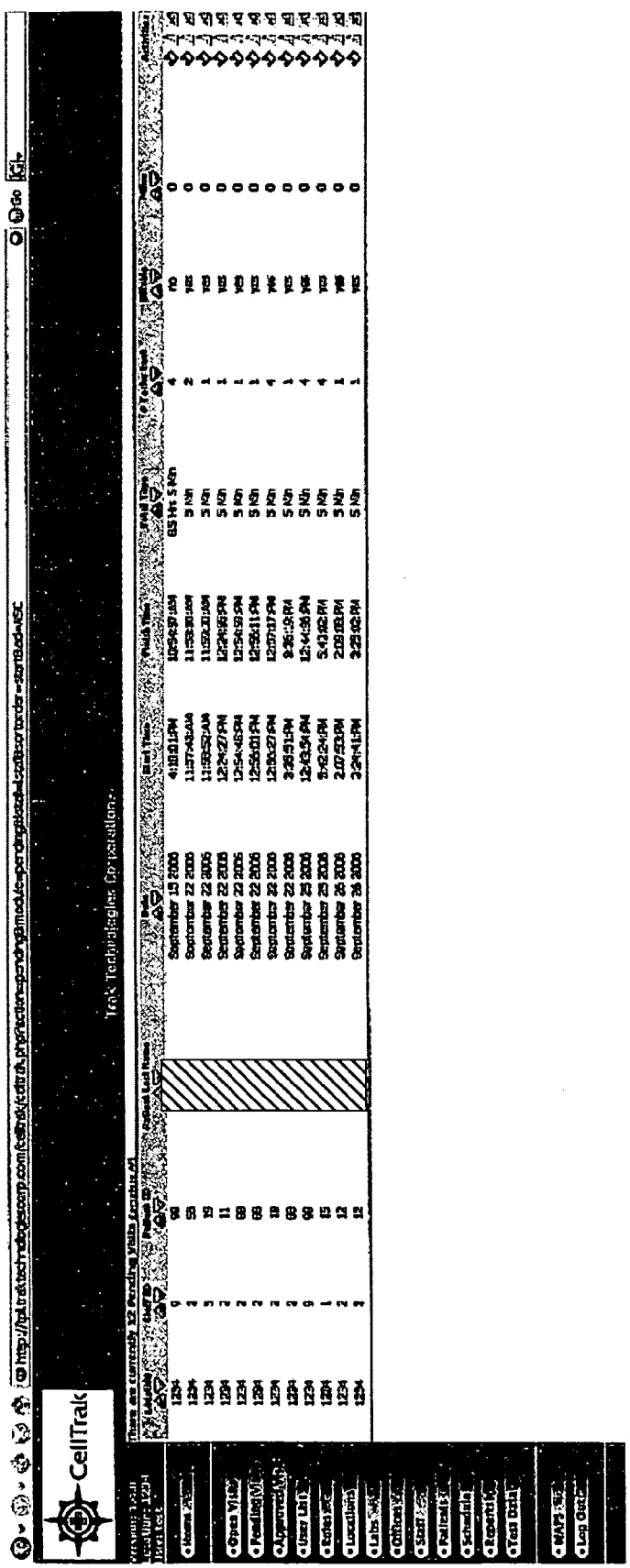
FIG. 15 shows a pictorial representation of a display screen for a web portal server computer, showing a "pending visits" summary screen, according to one embodiment of the invention.

FIG. 15 shows a pictorial representation of a display screen for a web portal server computer 114, showing a "pending visits" summary screen, according to one embodiment of the invention.

FIG. 16 shows a pictorial representation of a display screen for a web portal server computer 114, showing a "pending visits" details screen, according to one embodiment of the invention.

Figure 17:
FIG. 17 shows a pictorial representation of a display screen for a web portal server computer, showing an "approved visits" screen, according to one embodiment of the invention.

FIG. 17 shows a pictorial representation of a display screen for a web portal server computer 114, showing an "approved visits" screen, according to one embodiment of the invention.

Figure 18:
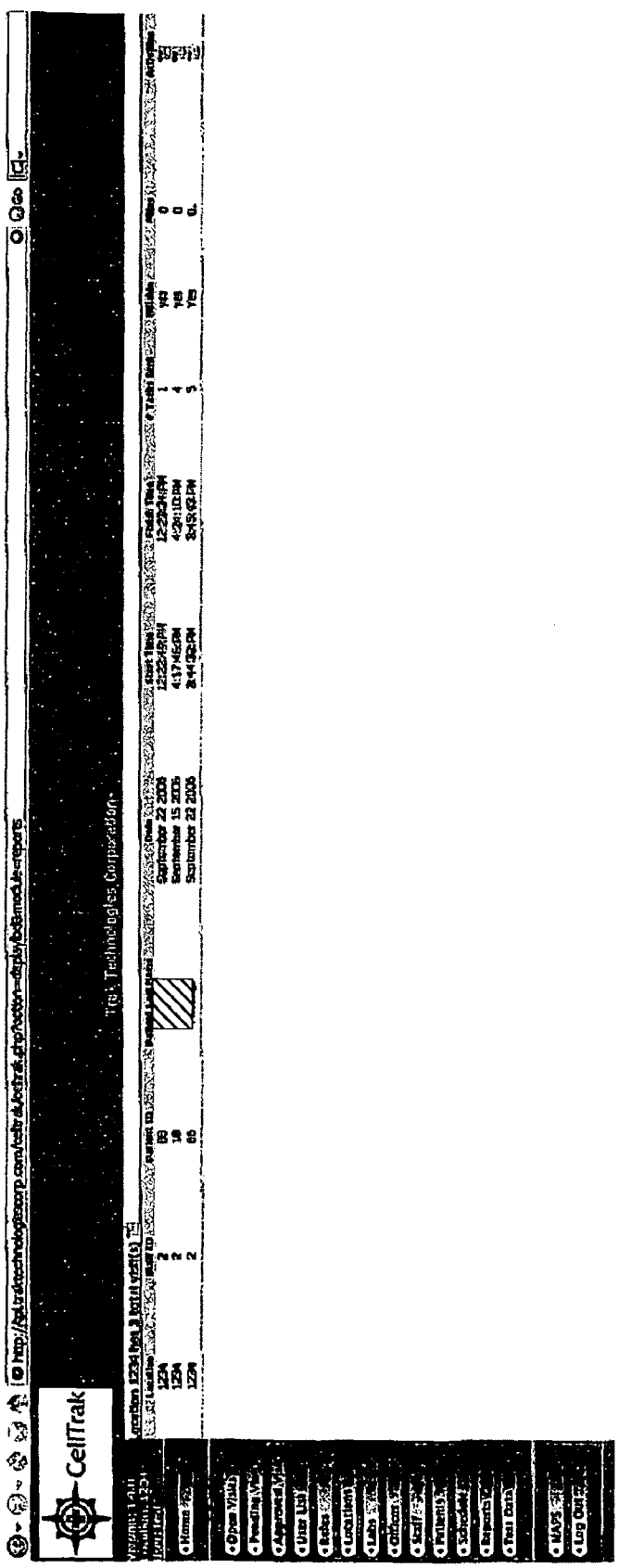
FIG. 18 shows a pictorial representation of a display screen for a web portal server computer, showing a "patient reports" summary screen, according to one embodiment of the invention.

FIG. 18 shows a pictorial representation of a display screen for a web portal server computer 114, showing a "patient reports" summary screen, according to one embodiment of the invention.

FIG. 19 shows a pictorial representation of a display screen for a web portal server computer 114, showing a sample patient report, according to one embodiment of the invention.

It should be understood that the illustrated embodiments are examples only and should not be taken as limiting the scope of the present invention. The claims should not be read as limited to the described order or elements unless stated to that effect. Therefore, all embodiments that come within the scope and spirit of the following claims and equivalents thereto are claimed as the invention.

We claim:

1. A home care administration system, comprising
   a server system accessible via a communication network, the server system comprising:
   a staff scheduling module for creating a work schedule for a plurality of caregivers. wherein the work schedule assigns each of the plurality of caregivers to a plurality of visits with a respective plurality of patients;
   a tracking and travel management module for determining visit e information for the plurality of caregivers, tracking visit times, and determining actual travel distance between visits by caregivers. wherein at least a portion of the work schedule created by the staff scheduling module is dynamically updated based on the tracked visit times;
   visit record and care plan module for administering visit records initiated by the caregivers during the visits and for designing patient-specific, visit-specific care plans comprising tasks to be performed during the visits; and
   a communication module for bidirectionally communicating care plans, scheduling information, and route information to
   a plurality of mobile devices via the communication network, wherein the plurality of mobile devices are associated with the respective plurality of caregivers scheduled to visit the respective plurality of patients, wherein the server system transmits the care plans to the mobile devices so that the associated caregivers receive information regarding tasks to be performed on the patients, and wherein the mobile devices are used by the caregivers to transmit back to the server system visit record information regarding performed tasks.

2. The home care administration system of claim 1, wherein each of the plurality of mobile devices comprises at least one application for rendering a fillable form based on a particular patient-specific, visit-specific care plan transmitted by the server system to the mobile device, wherein the caregiver enters data into the fillable form, and wherein a representation of the entered data is transmitted by the mobile device to the server system.

3. The home care administration system of claim 1, wherein communications between the server system and the plurality of mobile devices are encrypted.

4. The home care administration system of claim 2, wherein each of the plurality of mobile devices comprises data storage for temporarily storing the entered data if the mobile device is temporarily unable to communicate via the communication network, and wherein the temporarily stored entered data is transmitted to the communication network at a time when the mobile device is again able to communicate via the communication network.

5. The home care administration system of claim 1, wherein at least one of the plurality of mobile devices is a cell phone and wherein the communication network is a cellular network.

6. The home care administration system of claim 1, wherein at least one of the plurality of mobile devices includes a GPS receiver so that the location of the mobile device can be tracked, and wherein the location is transmitted from the mobile device to the tracking and travel management module of the server system.

7. The home care administration system of claim 6, wherein the tracking and travel management module uses the transmitted location to tracks the location of the caregiver associated with the mobile device.

8. The home care administration system of claim 7, wherein the tracking and travel management module determines an actual route traveled by the caregiver.

9. The home care administration system of claim 1, wherein the staff scheduling module creates the work schedule based on caregivers' respective locations.

10. The home care administration system of claim 1, wherein the visit record and care plan module collects and stores the visit record information and accepts a selection of tasks to be performed in a care plan for a particular patient.

11. The home care administration system of claim 1, wherein the server system further comprises a clinical messaging and notification module so that messages may be broadcast to the plurality of mobile devices.

12. The home care administration system of claim 1, wherein at least one of the mobile devices comprises an imaging device, wherein the mobile device transmits at least one image of a patient to the server system, and wherein the transmitted images may be used to remotely assess a condition of the patient.

13. The home care administration system of claim 12, wherein the caregiver associated with the mobile device records an annotation to accompany the at least one transmitted image.

14. The home care administration system of claim 1, wherein the mobile devices accept supply orders from the caregivers and transmit the supply orders to the server system for fulfillment.

15. The home care administration system of claim 1, wherein the server system further comprises a disease management intelligence module for applying rules to entered data transmitted from the mobile devices to the server system to determine whether additional action should be taken.

16. The home care administration system of claim 15, wherein the additional action comprises transmitting medical advice from the server system to the mobile device associated with the caregiver performing the visit from which the entered data originated.

17. The home care administration system of claim 1, wherein the server system includes an enterprise application integration module for integrating with a third-party application.

18. The home care administration system of claim 17, wherein the third-party application is selected from the group consisting of a billing system, a payroll system, and a scheduling system.

19. The home care administration system of claim 1, wherein the server system comprises at least one database storing information selected from the group consisting of patient demographic information, home care tasks, staff information, locations, visit records, visit status, care plans, actual tasks that are performed in each actual visit, clinical outcomes, and clinical measurements.

20. The home care administration system of claim 1, wherein the server system verifies that scheduled visits have actually occurred, based on comparing information from the staff scheduling module with information from the tracking and travel management module.

* * * * *